United States Patent [19]

Lüthy

[11] Patent Number: 4,584,295
[45] Date of Patent: Apr. 22, 1986

[54] PYRIMIDYLMETHYL THIOPHOSPHORUS ESTERS USEFUL FOR THE CONTROL OF INSECTS, MITES AND NEMATODES

[75] Inventor: Christoph Lüthy, Schwerzenbach, Switzerland

[73] Assignee: Hoffmann-La Roche Inc., Nutley, N.J.

[21] Appl. No.: 566,104

[22] Filed: Dec. 27, 1983

[30] Foreign Application Priority Data

Jan. 7, 1983 [CH] Switzerland ............................ 89/83
Nov. 18, 1983 [CH] Switzerland ........................ 6214/83

[51] Int. Cl.$^4$ ...................... A01N 57/16; C07F 9/65
[52] U.S. Cl. ...................................... 514/86; 544/243; 544/309; 544/315; 544/319; 544/326; 544/330; 544/334; 514/88
[58] Field of Search ...................... 544/243; 424/200; 514/86, 88

[56] References Cited

U.S. PATENT DOCUMENTS

| 3,185,699 | 5/1965 | Sherlock | 424/200 X |
| 4,326,058 | 4/1982 | Okabe et al. | 544/243 |
| 4,472,389 | 9/1984 | Dekeyser et al. | 424/200 |

FOREIGN PATENT DOCUMENTS

0087592 7/1981 Japan .................................. 544/243
0167696 12/1981 Japan .................................. 544/243
0091992 6/1982 Japan .................................. 424/200

OTHER PUBLICATIONS

Klicza et al., Chemical Abstracts, vol. 76, No. 17, 95726x (1971).

*Primary Examiner*—Donald G. Daus
*Assistant Examiner*—Diana G. Rivers
*Attorney, Agent, or Firm*—Jon S. Saxe; George M. Gould; John J. Maitner

[57] ABSTRACT

Heterocyclic compounds of the formula

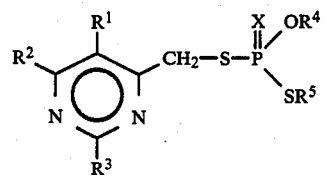

wherein $R^1$, $R^2$, $R^3$, $R^4$, $R^5$ and X are as defined hereinafter, process for their preparation, as well as pesticidal compositions containing these compounds as the active ingredient and methods for using the pesticidal compositions for the control of pests are described.

34 Claims, No Drawings

PYRIMIDYLMETHYL THIOPHOSPHORUS ESTERS USEFUL FOR THE CONTROL OF INSECTS, MITES AND NEMATODES

SUMMARY OF THE INVENTION

The invention is directed to heterocyclic compounds, especially pyrimidine derivatives of the formula

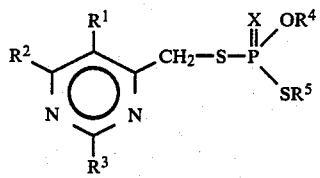

wherein $R^1$ is hydrogen, fluorine or chlorine, $R^2$ is hydrogen, fluorine, chlorine, $C_{1-4}$-alkyl, $C_{1-6}$-alkoxy, 2-propenyloxy, 2-propynyloxy, 2-($C_{1-4}$-alkoxy)-ethoxy, unsubstituted phenoxy, phenoxy monosubstituted or disubstituted with halogen, $C_{1-6}$-alkylthio, $C_{1-4}$-alkylamino, di($C_{1-4}$-alkyl)amino or a group (a) or (b)

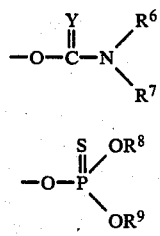

$R^3$ is hydrogen, fluorine, chlorine, $C_{1-6}$-alkyl, $C_{3-6}$-cycloalkyl, ($C_{1-4}$-alkoxy)methyl, ($C_{1-4}$-alkylthio)methyl, $C_{1-6}$-alkoxy, 2-propenyloxy, 2-propynyloxy, $C_{1-6}$alkylthio, $C_{1-4}$-alkylamino, di($C_{1-4}$-alkyl)amino or unsubstituted, monosubstituted or disubstituted phenyl, the substituents being fluorine, chlorine, trifluoromethyl and/or methoxy, $R^4$ is $C_{1-3}$-alkyl, $R^5$ is $C_{1-6}$-alkyl, $R^6$, $R^7$, $R^8$ and $R^9$ each independently are $C_{1-3}$-alkyl and X and Y each independently are oxygen or sulfur.

In another aspect, the invention relates to pesticidal compositions and methods of use. The compounds of formula I are particularly useful for the control of insects, mites and nematodes.

DETAILED DESCRIPTION OF THE INVENTION

The invention is directed to heterocyclic compounds, especially pyrimidine derivatives of the formula

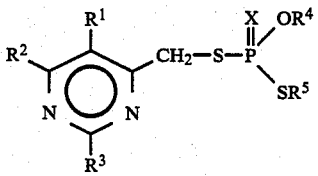

wherein $R^1$ is hydrogen, fluorine or chlorine, $R^2$ is hydrogen, fluorine, chlorine, $C_{1-4}$-alkyl, $C_{1-6}$-alkoxy, 2-propenyloxy, 2-propynyloxy, 2-($C_{1-4}$-alkoxy)-ethoxy, unsubstituted phenoxy, phenoxy monosubstituted or disubstituted with halogen, $C_{1-6}$-alkylthio, $C_{1-4}$-alkylamino, di($C_{1-4}$-alkyl)amino or a group (a) or (b)

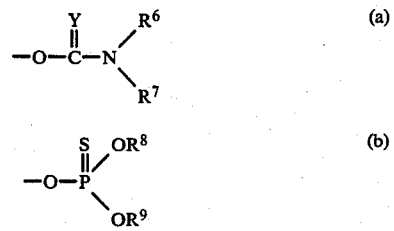

$R^3$ is hydrogen, fluorine, chlorine, $C_{1-6}$-alkyl, $C_{3-6}$-cycloalkyl, ($C_{1-4}$-alkoxy)methyl, ($C_{1-4}$-alkylthio)methyl, $C_{1-6}$-alkoxy, 2-propenyloxy, 2-propynyloxy, $C_{1-6}$-alkylthio, $C_{1-4}$-alkylamino, di($C_{1-4}$-alkyl)amino or unsubstituted, monosubstituted or disubstituted phenyl, the substituents being fluorine, chlorine, trifluoromethyl and/or methoxy, $R^4$ is $C_{1-3}$-alkyl, $R^5$ is $C_{1-6}$-alkyl, $R^6$, $R^7$, $R^8$ and $R^9$ each independently are $C_{1-3}$-alkyl and X and Y each independently are oxygen or sulfur.

As used herein the $C_{1-3}$-, $C_{1-4}$- and $C_{1-6}$-alkyl groups mentioned in the definition of the compounds of formula I encompass both straight-chain and branched-chain groups. This also applies to the $C_{1-4}$- and $C_{1-6}$-alkyl groups present in the 2-($C_{1-4}$-alkoxy)-ethoxy, $C_{1-4}$-alkylamino, di($C_{1-4}$-alkyl)amino, ($C_{1-4}$-alkoxy)methyl, ($C_{1-4}$-alkylthio)methyl, $C_{1-6}$-alkoxy and $C_{1-6}$-alkylthio groups. Under alkyl there are to be understood depending on the number of carbon atoms the following groups, for example: methyl, ethyl, n-propyl, isopropyl, n-butyl, isobutyl, tert.butyl, isoamyl and n-hexyl.

The term "halogen" denotes fluorine, chlorine, bromine and iodine, with fluorine and chlorine being preferred. In the phenoxy group monosubstituted or disubstituted with halogen the p-position and/or the m-position is preferably occupied.

Since the compounds of formula I can contain one or more asymmetric phosphorus atoms and/or one or more asymmetric carbon atoms, they can exist as optical antipodes. Formula I is, accordingly, intended to include the racemates as well as the separated optically active forms.

An interesting sub-class of compounds of formula I comprises those in which $R^2$ denotes hydrogen, fluorine, chlorine, $C_{1-4}$-alkyl, $C_{1-6}$-alkoxy, 2-propenyloxy, 2-propynyloxy, $C_{1-6}$-alkylthio, di($C_{1-4}$-alkyl)amino or a group (a) or (b), $R^3$ denotes hydrogen, fluorine, chlorine, $C_{1-6}$-alkyl, $C_{3-6}$-cycloalkyl, ($C_{1-4}$-alkoxy)methyl, ($C_{1-4}$-alkylthio)methyl, $C_{1-6}$-alkoxy, 2-propenyloxy, 2-propynyloxy, $C_{1-6}$-alkylthio, di($C_{1-4}$-alkyl)amino or unsubstituted, monosubstituted or disubstituted phenyl, the substituents being fluorine, chlorine, trifluoromethyl and/or methoxy, and $R^1$, $R^4$, $R^5$ and X are as described previously.

Independently of one another $R^1$ preferably denotes hydrogen or chlorine, especially hydrogen, $R^2$ preferably denotes $C_{1-3}$-alkoxy, 2-propynyloxy, phenoxy, $C_{1-3}$-alkylthio or a group (a), especially methoxy, ethoxy, isopropoxy or 2-propynyloxy, $R^3$ preferably denotes hydrogen; $C_{1-6}$-alkyl, especially methyl, isopropyl or tert.butyl; $C_{3-6}$-cycloalkyl, especially cyclopropyl; $C_{1-6}$-alkoxy, especially methoxy or ethoxy; $C_{1-6}$-alkylthio, especially methylthio or ethylthio; $C_{1-4}$-alkylamino, especially isopropylamino; or di($C_{1-4}$-alkyl)amino, especially dimethylamino or diethylamino, $R^4$ preferably denotes ethyl, $R^5$ preferably denotes n-propyl or sec.butyl, especially n-propyl, $R^6$ and $R^7$ each preferably denote methyl, $R^8$ and $R^9$ preferably denote methyl or ethyl, and X and Y each preferably denote oxygen.

Preferred compounds of formula I are:

O-Ethyl S-(2,6-diethoxy-4-pyrimidinylmethyl) S-(n-propyl)dithiophosphate and

O-ethyl S-[2-isopropyl-6-(2-propynyloxy)-4-pyrimidinylmethyl] S-(n-propyl)dithiophosphate.

Further representative compounds of formula I are:

O-Ethyl S-(2-cyclopropyl-6-methylthio-4-pyrimidinylmethyl) S-(n-propyl)dithiophosphate, O-ethyl S-(6-ethylthio-2-methyl-4-pyrimidinylmethyl) S-(n-propyl)dithiophosphate, O-ethyl S-(6-chloro-2-cyclopropyl-4-pyrimidinylmethyl) S-(n-propyl)dithiophosphate, O-ethyl S-(2-cyclopropyl-6-isopropoxy-4-pyrimidinylmethyl) S-(n-propyl)dithiophosphate, O-ethyl S-[2-cyclopropyl-6-(2-propenyloxy)-4-pyrimidinylmethyl] S-(n-propyl)dithiophosphate, O-ethyl S-[2-cyclopropyl-6-(2-propynyloxy)-4-pyrimidinylmethyl] S-(n-propyl)dithiophosphate, S-(2-ethoxy-6-methyl-4-pyrimidinylmethyl) O-ethyl S-(n-propyl)dithiophosphate, S-(6-ethoxy-2-methyl-4-pyrimidinylmethyl) O-methyl S-(n-propyl)dithiophosphate, O-ethyl S-(2,6-diethoxy-4-pyrimidinylmethyl) S-isopropyl dithiophosphate, O-ethyl S-(n-butyl) S-(2,6-diethoxy-4-pyrimidinylmethyl)dithiophosphate, S-(6-ethoxy-5-chloro-2-methyl-4-pyrimidinylmethyl) O-ethyl S-(n-propyl)dithiophosphate, O-ethyl S-(5-chloro-2-isopropyl-6-ethoxy-4-pyrimidinylmethyl) S-(n-propyl)dithiophosphate, O-ethyl S-(6-ethylthio-2-isopropyl-4-pyrimidinylmethyl) S-(n-propyl)dithiophosphate, O-ethyl S-(2,6-dimethyl-4-pyrimidinylmethyl) S-(n-propyl)dithiophosphate, S-(2-ethoxy-6-methoxy-4-pyrimidinylmethyl) O-ethyl S-(n-propyl)dithiophosphate, O-ethyl S-(6-dimethylcarbamoyloxy-2-isopropyl-4-pyrimidinylmethyl) S-(n-propyl)dithiophosphate, O-ethyl S-(2-cyclopropyl-6-dimethylcarbamoyloxy-4-pyrimidinylmethyl) S-(n-propyl)dithiophosphate, O-ethyl S-(6-dimethylcarbamoyloxy-2-methoxy-4-pyrimidinylmethyl) S-(n-propyl)dithiophosphate, O-ethyl S-[6-(O,O-diethyl-thiophosphoro)-2-isopropyl-4-pyrimidinylmethyl] S-(n-propyl)dithiophosphate, O-ethyl S-[6-(O,O-dimethyl-thiophosphoro)-2-diethylamino-4-pyrimidinylmethyl] S-(n-propyl)dithiophosphate, O-ethyl S-(2-cyclopropyl-6-fluoro-4-pyrimidinylmethyl) S-(n-propyl)dithiophosphate, S-(2-ethoxy-6-fluoro-4-pyrimidinylmethyl) O-ethyl S-(n-propyl)dithiophosphate, O-ethyl S-(6-methoxy-2-methoxymethyl-4-pyrimidinylmethyl) S-(n-propyl)dithiophosphate, S-(6-ethoxy-2-phenyl-4-pyrimidinylmethyl) O-ethyl S-(n-propyl)dithiophosphate, O-ethyl S-[6-(O,O-dimethyl-thiophosphoro)-2-ethyl-4-pyrimidinylmethyl] S-(n-propyl)dithiophosphate, S-(2-ethoxy-6-isopropoxy-4-pyrimidinylmethyl) O-ethyl S-(n-propyl)dithiophosphate, S-(2-ethoxy-4-pyrimidinylmethyl) O-ethyl S-(n-propyl)dithiophosphate, O-ethyl S-(2-diethylamino-6-methyl-4-pyrimidinylmethyl) S-(n-propyl)dithiophosphate, S-(2-ethoxy-6-methylthio-4-pyrimidinylmethyl) O-ethyl S-(n-propyl)dithiophosphate, S-(2-ethoxy-6-isopropylthio-4-pyrimidinylmethyl) O-ethyl S-(n-propyl)dithiophosphate, S-(2,6-diethoxy-4-pyrimidinylmethyl) O,S-di(n-propyl)-dithiophosphate, O-ethyl S-(6-fluoro-4-pyrimidinylmethyl) S-(n-propyl)-dithiophosphate, O-ethyl S-(6-methyl-2-methoxy-4-pyrimidinylmethyl) S-(n-propyl)dithiophosphate, S-(6-ethoxy-2-isopropoxy-4-pyrimidinylmethyl) O-ethyl S-(n-propyl)dithiophosphate, S-(6-ethoxy-2-ethylthio-4-pyrimidinylmethyl) O-ethyl S-(n-propyl)dithiophosphate, S-(6-ethoxy-2-dimethylamino-4-pyrimidinylmethyl) O-ethyl S-(n-propyl)dithiophosphate, S-(6-ethoxy-5-chloro-2-methylthio-4-pyrimidinylmethyl) O-ethyl S-(n-propyl)dithiophosphate, O-ethyl S-(5-chloro-6-isopropoxy-2-methoxy-4-pyrimidinylmethyl) S-(n-propyl)dithiophosphate, O-ethyl S-(n-propyl) S-(4-pyrimidinylmethyl)dithiophosphate, S-(2-ethoxy-6-chloro-4-pyrimidinylmethyl) O-ethyl S-(n-propyl)dithiophosphate, O-ethyl S-(6-chloro-2-methoxy-4-pyrimidinylmethyl) S-(n-propyl)dithiophosphate, O-ethyl S-(2-chloro-6-isopropoxy-4-pyrimidinylmethyl) S-(n-propyl)dithiophosphate and S-[2-ethoxy-6-(2-methoxyethoxy)-4-pyrimidinylmethyl] O-ethyl S-(n-propyl)dithiophosphate.

The compounds of formula I are prepared by one of the following procedures.

(A) Reacting a pyrimidine derivative of the formula

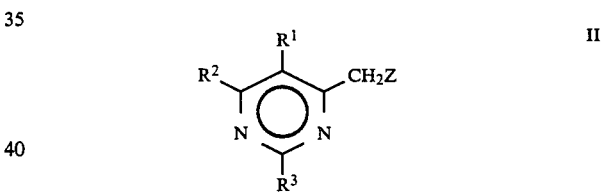

wherein $R^1$, $R^2$ and $R^3$ are as described previously, and Z denotes a leaving group such as chlorine, bromine, iodine, mesyloxy or tosyloxy, with a dithiophosphate or trithiophosphate of the formula

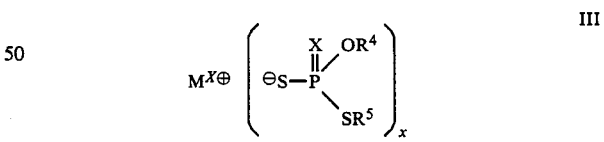

wherein $R^4$, $R^5$ and X are as described previously, $M^{x\oplus}$ stands for an alkali metal, alkaline earth metal or optionally substituted ammonium ion and x signifies the valency of the cation $M^{x\oplus}$.

This reaction is conveniently carried out in the presence of an inert diluent, especially an inert organic solvent such as a lower aliphatic alcohol (e.g. methanol or ethanol), a lower aliphatic ketone (e.g. acetone or methyl ethyl ketone), an aliphatic or cyclic ether (e.g. diethyl ether, glycol methyl ether, glycol dimethyl ether, tetrahydrofuran or dioxan), a halogenated hydrocarbon (e.g. methylene chloride, chloroform or 1,1,1-trichloroethane), a lower aliphatic ester (e.g. ethyl acetate), a lower aliphatic nitrile (e.g. acetonitrile), a formamide (e.g. dimethylformamide) or an aromatic hydrocarbon (e.g. benzene or toluene), or water.

The reaction temperatures can vary in a wide range, but the reaction is generally carried out at a temperature between 0° C. and the reflux temperature of the reaction mixture, preferably between room temperature and 70° C., especially between 35° C. and 50° C.

If a pyrimidine derivative of formula II in which Z denotes chlorine is used as the starting material, then the reaction can be accelerated by the addition of a catalytic amount of an alkali metal iodide, for example sodium or potassium iodide (Finkelstein reaction), or of a copper or silver salt, for example copper (I) chloride, copper (II) chloride or silver acetate.

Examples of alkali metal salts and alkaline earth metal salts of formula III which can be used in this reaction are the sodium and potassium salt and the calcium salt. The substituted ammonium ion can be, for example, mono-, di- or tri(lower alkyl)ammonium such as tert.butylammonium, dimethylammonium or dimethylethyl-ammonium.

(B) Treating a pyrimidine derivative of the formula

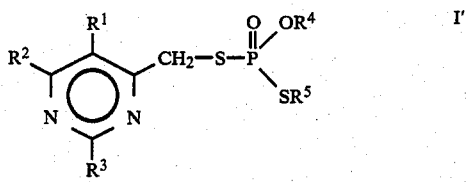

wherein $R^1$, $R^2$, $R^3$, $R^4$ and $R^5$ are as described previously, with the exception of the derivatives of formula I' in which $R^2$ denotes

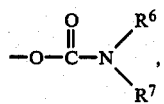

with a sulfurizing agent.

This procedure leads to compounds of formula I in which X denotes sulfur. For the sulfurization of the derivatives of formula I' there can be used sulfurizing agents such as phosphorus pentasulfide, alone or in the presence of pyridine, the phosphorus pentasulfide-pyridine (1:2) complex and the dimer of p-methoxyphenylthiophosphine sulphide [see e.g. S.-O. Lawesson et al., Bull. Soc. Chim. Belg. 87, 229–238 (1978)]. The reaction is advantageously carried out in an inert organic diluent such as an aromatic (e.g. toluene, a xylene or pyridine) or hexamethylphosphoric acid triamide. The reaction temperatures conveniently lie between room temperature and the boiling point of the reaction mixture, preferably between room temperature and 80° C., especially between 45° C. and 60° C.

The isolation and the purification of the compounds of formula I can be carried out using conventional techniques well known in the art.

The above noted procedures produce products consisting of a mixture of two or more optical isomers. The isomers can be separated by methods well known in the art. If desired, the optical isomers can be prepared by using corresponding optically active starting materials.

The pyrimidine derivatives of formula II used as starting materials are either known or can be produced according to methods known per se; for example, according to T. Sakamoto et al., Chem. Pharm. Bull. 28, 3362–3368 (1980), DOS No. 2,703,310 and DOS No. 3,003,337. In particular, there are known 4-chloromethyl-2-isopropyl-6-methylpyrimidine (Chem. Pharm. Bull. 28, 3363), O-(6-chloromethyl-2-methoxymethyl-4-pyrimidinyl) O,O-dimethyl thiophosphate and O-(6-chloromethyl-2-methoxymethyl-4-pyrimidinyl) O,O-diethyl thiophosphate [DOS No. 3,003,337, p. 11, compounds (17) and (18)], the production of these compounds being described in these literature references. The 4-halomethyl-2,6-dialkyl-pyrimidines and O-(2-alkoxymethyl or alkylthiomethyl-6-halomethyl-4-pyrimidinyl) O,O-dialkyl thiophosphates can in general be produced in accordance with the processes described therein. Moreover, those starting materials of formula II in which $R^1$ signifies hydrogen, $R^2$ signifies a group (b), $R^3$ signifies hydrogen, $C_{1-6}$-alkyl, $C_{1-6}$-alkoxy, $C_{1-6}$-alkylthio or $C_{1-4}$-alkylamino and Z signifies chlorine, bromine or iodine can be produced according to the process described in DOS No. 2,703,310.

A process for the production of those starting materials of formula II in which $R^1$ signifies hydrogen or chlorine, one of $R^2$ and $R^3$ signifies fluorine and the other signifies chlorine, and Z signifies chlorine is known from DOS No. 3,118,700.

Those starting materials of formula II in which $R^2$ and/or $R^3$ signifies $C_{1-6}$-alkoxy, 2-propenyloxy or 2-propynyloxy can be produced, for example, by direct alkylation, alkenylation or alkynylation of the corresponding 2-hydroxy-, 6-hydroxy- or 2,6-dihydroxy-4-methyl-pyrimidine derivative of the general formula

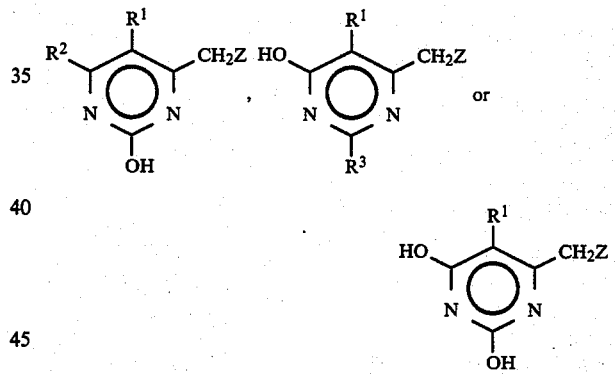

wherein $R^1$, $R^2$, $R^3$ and Z have the significances given above.

Suitable alkylating, alkenylating and alkynylating agents are the corresponding aliphatic sulphates such as dialkyl sulphates (e.g. dimethyl sulphate and diethyl sulphate), aliphatic halides (e.g. ethyl iodide, allyl bromide and propargyl bromide) and Meerwein salts (e.g. triethyloxonium tetrafluoroborate and trimethyloxonium tetrafluoroborate). Moreover, a diluent, especially an organic solvent such as a ketone (e.g. acetone), a nitrile (e.g. acetonitrile), an aliphatic or cyclic ether (e.g. diethyl ether, tetrahydrofuran or dioxan), a formamide (e.g. dimethylformamide) or N-methylpyrrolidone, and an acid-binding agent, especially a base (e.g. sodium hydride, sodium hydroxide, sodium carbonate, potassium carbonate, potassium tert.butylate or triethylamine), are conveniently used. If desired, the reaction can also be carried out in a two-phase system such as sodium hydroxide solution/chloroform or potassium hydroxide solution/toluene. The alkylation, alkenylation or alkynylation is generally carried out at a temperature between 0° C. and the reflux temperature of the reaction mixture. If the alkylation is carried out with a Meerwein salt, then the reaction is preferably carried out in a melt or at the reflux temperature of the reaction mixture, the solvent being preferably a halogenated hydrocarbon, especially methylene chloride, 1,1,2-trichloroethane or chlorobenzene.

Instead of the above-mentioned direct alkylation, alkenylation or alkynylation of the 2-hydroxy-, 6-hydroxy- or 2,6-dihydroxy-4-methyl-pyrimidine derivative, this can firstly be converted into the corresponding 2-chloro-, 6-chloro- or 2,6-dichloro-4-methyl-pyrimidine derivative and the chlorinated product can thereupon be reacted with a $C_{1-6}$-alkanol, 2-propenol or 2-propynol, conveniently in the presence of sodium or in the form of the corresponding sodium alkoxide, alkenoxide or alkynoxide, to form the desired pyrimidine derivative of formula II in which $R^2$ and/or $R^3$ signifies $C_{1-6}$-alkoxy, 2-propenyloxy or 2-propynyloxy. The 6-chloro-4-methyl-pyrimidine derivative can be reacted with a 2-($C_{1-4}$-alkoxy)-ethanol or an optionally halogenated phenol in an analogous manner in order to produce the desired pyrimidine derivative of formula II in which $R^2$ signifies 2-($C_{1-4}$-alkoxy)-ethoxy or phenoxy optionally substituted with halogen. The chlorination and the etherification can be carried out under reaction conditions which are familiar to the person skilled in the art (see, for example, European Patent Publication No. 15,078).

Those starting materials of formula II in which $R^2$ and/or $R^3$ signifies $C_{1-6}$-alkylthio can also be produced from the corresponding 2-chloro-, 6-chloro- or 2,6-dichloro-4-methyl-pyrimidine derivatives by reacting the latter with a $C_{1-6}$-alkylmercaptan. This reaction can be carried out under reaction conditions which are familiar to the person skilled in the art, especially using a diluent and a base, as mentioned above in the case of the alkylation of 2-hydroxypyrimidine derivatives, and at temperatures between 0° C. and the reflux temperature of the respective reaction mixture. If Z in formula II signifies chlorine, bromine or iodine, then the group —$CH_2Z$ is firstly protected, preferably by replacing the residue Z with an acyloxy group, especially an acetoxy group. After the treatment with the $C_{1-6}$-alkylmercaptan the protecting group is removed and the group —$CH_2Z$ is regenerated according to methods known per se. For example, the optionally 2($R^3$)- and/or 5($R^1$)-substituted 4-chloromethyl-6-hydroxy-pyrimidine is converted with sodium acetate and a catalytic amount of sodium iodide in glacial acetic acid into the corresponding 4-acetoxymethyl-pyrimidine derivative and this is subsequently chlorinated using phosphorus oxychloride. The resulting protected 6-chloro-pyrimidine derivative is then treated with the $C_{1-6}$-alkylmercaptan. In order to remove the protecting group the 4-acetoxymethyl-6-alkylthio-pyrimidine derivative is treated with sodium hydroxide in ethanol. Finally, in order to transform the 4-hydroxymethyl group generated in the preceding step into the desired chloromethyl group it is treated with thionyl chloride.

Analogously to the process described above for the production of the starting materials of formula II containing $C_{1-6}$-alkylthio groups, the 2-chloro-, 6-chloro- and 2,6-dichloro-4-methyl-pyrimidine derivatives can be reacted with a $C_{1-4}$-alkylamine or a di($C_{1-4}$-alkyl)amine to give corresponding starting materials of formula II in which $R^2$ and/or $R^3$ signifies $C_{1-4}$-alkylamino or di($C_{1-4}$-alkyl)amino. In this case the use of an additional base is unnecessary having regard to the basic character of the $C_{1-4}$-alkylamine or di($C_{1-4}$-alkyl)amine.

The starting materials of formula II in which $R^2$ signifies $C_{1-4}$-alkyl, $R^3$ signifies $C_{1-6}$-alkyl, $C_{3-6}$-cycloalkyl, ($C_{1-4}$-alkoxy)methyl, $C_{1-6}$-alkoxy, di($C_{1-4}$-alkyl)amino or phenyl optionally substituted with methoxy and Z signifies chlorine can be produced by converting the corresponding 2-substituted 4-alkyl-6-hydroxy-pyrimidine by chlorination into the corresponding 6-chloro-pyrimidine derivative, reducing this by means of zinc/mineral acid to the corresponding 6-unsubstituted pyrimidine derivative, treating the 2-substituted 4-alkyl-pyrimidine with ammonium peroxydisulphate in the presence of methanol and dilute sulphuric acid and finally chlorinating the product, i.e. the corresponding 2-substituted 4-alkyl-6-hydroxymethyl-pyrimidine, using phosphorus oxychloride or thionyl chloride in order to give the desired 2-substituted 4-alkyl-6-chloromethyl-pyrimidine. The last two steps of this synthesis are specifically exemplified in Chem. Pharm. Bull. 28, 3362–3368 (1980).

Those starting materials of formula II in which $R^1$ signifies chlorine can be produced by direct chlorination of the corresponding 5-unsubstituted pyrimidine derivative. For this purpose there come into consideration as the chlorinating agent especially elemental chlorine, sulphuryl chloride and N-chlorosuccinimide. The chlorination is conveniently carried out in the presence of an inert diluent such as a halogenated hydrocarbon (e.g. methylene chloride), acetic acid or water at temperatures between −20° C. and 60° C., preferably between 0° C. and 45° C. Even when the 2-position and/or the 4-position of the pyrimidine nucleus is unoccupied, i.e. when $R^3$ and/or $R^2$ signifies hydrogen, only the 5-position is chlorinated under the reaction conditions which are familiar to the person skilled in the art. From the above-mentioned 2-hydroxy-, 6-hydroxy- or 2,6-dihydroxy-4-methyl-pyrimidine derivative in which the 5-position is unoccupied there can also be produced by such a chlorination the corresponding 5-chloro compound, and this can then be further reacted in the manner described above in order to produce starting materials of formula II containing alkoxy, 2-propenyloxy, 2-propynyloxy or alkylthio groups.

For the production of those starting materials of formula II in which $R^1$, $R^2$ and/or $R^3$ signifies hydrogen the corresponding compounds of formula II in which $R^1$, $R^2$ and/or $R^3$ signifies chlorine can be reduced with zinc/mineral acid under reaction conditions which are familiar to the person skilled in the art. If Z in formula II signifies chlorine, bromine or iodine, then the group —$CH_2Z$ is firstly protected, preferably by replacing Z by an acyloxy group, especially acetoxy, the protecting group is removed after the reductive treatment and then the group —$CH_2Z$ is regenerated. These additional reaction steps can be carried out according to methods known per se, as given above.

For the production of the starting materials of formula II in which $R^1$ and/or $R^2$ signifies fluorine the corresponding chlorine-containing compounds can be reacted with sodium fluoride or potassium fluoride in order to replace chlorine by fluorine. The reaction is conveniently carried out in the presence of an anhydrous diluent such as an aromatic hydrocarbon (e.g. a xylene), a lower aliphatic nitrile (e.g. acetonitrile), tetramethylene sulphone, dimethyl sulphoxide, dimethylformamide or 1,3-dimethyl-2-imidazolidinone at temperatures between about 70° C. and the boiling point of the reaction mixture, preferably between about 80° C. and 140° C. Moreover, the reaction is conveniently carried out with the aid of a phase transfer catalyst such as a polyethylene ether-crown compound, for example 15-crown-5 (polyethylene ether-crown compound with a 15-ring containing 5 oxygen atoms).

For the production of the starting materials of formula II in which $R^3$ signifies fluorine the corresponding chlorine-containing compounds can be treated with anhydrous hydrofluoric acid in order to replace chlorine with fluorine. The reaction can be conveniently carried out by also using the hydrofluoric acid as the solvent in an autoclave under elevated pressure as is described, for example, in DOS. No. 3,118,700.

Further possibilities for the production of starting materials of formula II are the carbamoylation and the phosphorylation of the above-mentioned 6-hydroxy-4-methylpyrimidine derivatives with dialkyl(thio)carbamoyl halides and thiophosphoric acid ester halides, respectively, of the general formulae

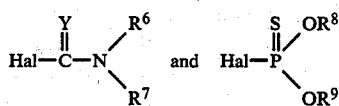

wherein $R^6$, $R^7$, $R^8$, $R^9$ and Y have the significances given above and Hal stands for halogen, especially for chlorine, to give the corresponding pyrimidine derivatives of formula II in which $R^2$ signifies a group (a) or (b). The carbamoylation and the phosphorylation can also be carried out under reaction conditions which are familiar to the person skilled in the art.

The 2-hydroxy-, 6-hydroxy- and 2,6-dihydroxy-4-methyl-pyrimidine derivatives which are required for the production of these starting materials II are either known or can be produced according to methods known per se. Among such derivatives which are known there can be mentioned, for example, 4-chloromethyl-uracil [see Angew. Chem. 80, 405–406 (1968)], 2-isopropyl-, 2-methyl-, 2-isopropyl-5-chloro-, 2-phenyl- and 2-methyl-5-chloro-4-hydroxy-6-chloromethylpyrimidine as well as 6-chloromethyl-pyrimidinol (see DOS No. 2,167,194) and 4-chloromethyl-6-hydroxy-2-methylthiopyrimidine [see J. Org. Chem. 27, 3545–3549 (1962)].

The 2-alkyl-5-chloro-4-chloromethyl-6-hydroxy-pyrimidines and the corresponding 2- and/or 5-unsubstituted pyrimidine derivatives are generally obtainable by the process described in DOS No. 2,167,194. The production of 4-chloromethyl-6-hydroxy-2-methylthio-pyrimidine is described in J. Org. Chem. 27, 3549 (1962). The hitherto unknown 2-alkoxy- and 2-dialkylamino-4-chloromethyl-6-hydroxy-pyrimidines and 4-chloromethyl-6-hydroxy-pyrimidine can be produced in an analogous manner, namely from the corresponding O-alkylisourea, N,N-dialkylguanidine or formamidine or a salt thereof and $\gamma$-chloroacetoacetyl chloride or an alkyl $\gamma$-chloroacetoacetate, especially methyl or ethyl $\gamma$-chloroacetoacetate.

The dithiophosphates and trithiophosphates of formula III used as starting materials are either known or can be produced according to methods known per se; for example, in accordance with Houben-Weyl, Vol. XII/2, p. 689–690 and DOS No. 2,506,618.

The starting materials of formula I' are those pyrimidine derivatives of formula I in which X signifies oxygen, with the exception of such derivatives in which $R^2$ signifies

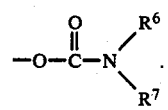

The compounds of formula I are quite generally of value as pesticides. They have been found to be especially valuable for the control of insects, mites and nematodes, especially of Coleoptera such as, for example, Epilachna spp., Leptinotarsa decemlineata, Anthonomus spp., Conotrachelus nenuphar, Lema spp., Lissorhoptrus oryzaephilus, Phyllotreta spp., Psylliodes chrysocephala, Melingetes aenus, Ceutorrhynchus assimilis, Otiorhynchus sulcatus, Melolontha melolontha and Diabrotica spp.

Lepidoptera such as, for example, Laspeyresia spp., Adoxophyes orana, Tortrix viridana, Cheimatobia brumata, Lyonetia clerkella, Operophtera brumata, Lithocolletis blancardella, Ephestia kuehniella, Mamestra brassicae, Agrotis segetum, Plutella spp., Pieris brassicae, Choristoneura fumiferana, Heliothis spp., Spodoptera spp., Earias insulana, Pectinophora gossipiella, Chilo spp., Ostrinia nubilalis, Clysia ambiguella, Lobesia botrana.

Diptera such as, for example Drosophila melanogaster, Ceratitis spp., Oscinella frit, Dacus spp. and Rhagoletis spp., leatherjacket spp., Sciara spp. and Phorbia spp.

Homoptera, i.e. aphids such as, for example, Aphis fabae, Myzus persicae and other species of these genera, Rhophalosiphon spp., Schizaphis spp. as well as scale insects and mealy bugs such as, for example, Saissetia spp., Quadraspidiotus perniciosus, Aonidiella aurantii, Planococcus spp. as well as cleades such as, for example, Nephotettix spp., Laodelphax spp. and Nilaparvata spp., Alurodidae such as, for example, Trialeurodes vaporariorum, Bemisia spp., furthermore, species of thrips.

Heteroptera such as, for example, Dysdercus spp. and Lygus spp.

Acarina such as, for example, Tetranychus urticae, Panonychus ulmi and other Tetranychidae, Eriophyidae such as Phyllocoptruta oleivora, Aceria sheldoni, Eriophyes spp., Aceria spp. and, further, ticks.

Nematoda such as, for example, free-living nematodes (inter alia Pratylenchus spp. such as P. penetrans), leaf-parasitic nematodes (inter alia Aphelenchoides) and root-parasitic nematodes (inter alia meloidogynae spp. such as M. incognita, Globodera spp. such as G. rostochiensis).

The heterocyclic compounds of formula I are active as pesticides which function both as contact and feed poisons. In addition, some of the compounds are taken up by various plants, so that the pests to be controlled are exterminated upon eating the plants. These compounds thus exhibit systemic activity.

The invention is also directed to pesticidal compositions which comprise inert carrier material and, as the active ingredient, a compound of formula I. These compositions conveniently contain, as the inert carrier material, at least one of the following ingredients: solid carrier materials; solvents or dispersion media; surface active agents, for example, wetting and emulsifying agents; dispersing agents (without tenside action); and stabilizers.

Examples of solid carrier materials include natural mineral substances, such as kaolin, aluminas, siliceous earth, talc, bentonite, chalk, limestone, quartz, dolomite, attapulgite, montmorillonite and diatomaceous earth; synthetic mineral substances, such as highly dispersible silicic acid, aluminum oxide and silicates; organic substances, such as cellulose, starch, urea and synthetic resins; and fertilizers, such as phosphates and nitrates, whereby such carrier substances can be present, for example, as dusts, powders, or granulates.

Examples of liquid solvents or dispersion media include: aromatics, such as toluene, xylenes, benzene and alkylnaphthalenes; chlorinated aromatics and chlorinated aliphatic hydrocarbons, such as chlorbenzenes, chloroethylenes and methylene chloride; aliphatic hydrocarbons, such as cyclohexane and paraffins (e.g., petroleum fractions); alcohols, such as butanol and glycol, as well as their ethers and esters; ketones, such as acetone, methyl ethyl ketone, methyl isobutyl ketone and cyclohexanone; and strongly polar solvents, such as dimethylformamide, N-methylpyrrolidone and dimethylsulfoxide, whereby such solvents or dispersion media preferably have flash points of at least 30° C. and boiling points of at least 50° C., and water. When water is used as the solvent, organic solvents can also be used as auxiliary solvents.

Included among the solvents or dispersion media are the so-called liquified gaseous extenders or carrier substances. By liquified gaseous extenders or carrier substances are meant liquids which are gaseous at normal temperature and under normal pressure, such as aerosol propellants, e.g., halogenated hydrocarbons (e.g., dichlorodifluoromethane).

Surface active agents, especially emulsifying agents and wetting agents, suitable for use in the pesticidal compositions of this invention can be non-ionic, anionic, or cation compounds.

Examples of non-ionic compounds which can be used include condensation products of fatty acids, fatty alcohols, or fatty-substituted phenols with ethylene oxide; fatty acid esters and ethers of sugars or polyvalent alcohols; the products which are obtained from sugars or polyvalent alcohols by condensation with ethylene oxide; block polymers of ethylene oxide and propylene oxide; or alkyldimethylamine oxides.

Examples of anionic compounds include soaps; fatty sulfate esters, such as dodecyl sodium sulfate, octadecyl sodium sulfate, and cety sodium sulfate; alkyl sulfonates, aryl sulfonates, and fatty-aromatic sulfonates, such as alkylbenzene sulfonates, for example, calcium dodecylbenzene sulfonate and butylnaphthalene sulfonates; and more complex fatty sulfonates, for example, the amide condensation products of oleic acid and N-methyltaurine and the sodium sulfonate of dioctyl succinate.

Examples of cationic compounds include alkyldimethylbenzylammonium chloride, dialkyldimethylammonium chlorides, alkyltrimethylammonium chlorides and ethoxylated quaternary ammonium chlorides.

Dispersing agents suitable for use in the pesticidal compositions of this invention are lignin, sodium and ammonium salts of lignin sulfonic acid, sodium salts of maleic acid anhydride-diisobutylene copolymers, sodium and ammonium salts of sulfonated polycondensation products of naphthalene and formaldehyde, and sulfite lyes. Dispersing agents, which are especially suitable as thickening or anti-settling agents, include methylcellulose, carboxymethylcellulose, hydroxyethylcellulose, polyvinyl alcohol, alginates, caseinates and blood albumin.

Stabilizers suitable for use in the pesticidal compositions of the present invention include acid-binding agents, such as epichlorohydrin, phenyl glycidyl ether and soya epoxides; antioxidants, such as gallic acid esters and butylhydroxytoluene; UV-absorbers, such as substituted benzophenones, diphenylacrylonitrile acid esters and cinnamic acid esters; and deactivators, such as salts of ethylenediaminotetraacetic acid and polyglycols.

The pesticidal compositions of this invention can contain, in addition to the active substances of formula I, other active substances, such as other pest control agents, pest baits, fungicides, bactericides, herbicides, plant growth regulators and fertilizers. Such combination compositions are suitable for increasing the activity or for broadening the spectrum of activity. If necessary, inadequacies of known compositions can thereby also be compensated for.

The pesticidal compositions of the present invention can be prepared by known methods, for example, by mixing the active ingredient with solid carrier materials, by dissolution or suspension in suitable solvents or dispersion media, and, if necessary, using surface active agents, as wetting or emulsifying agents, or dispersing agents, or by diluting pre-prepared emulsifiable concentrates with solvents or dispersion media.

In preparing the pesticidal compositions of the present invention, the active ingredient of formula I is mixed with inert carrier material. In the case of pulverous composition, the active ingredient can be mixed with the solid carrier material, for example, by milling together, or the solid carrier material can be impregnated with a solution or suspension of the active ingredient and then the solvent or suspension medium can be removed by evaporation, heating or removing under reduced pressure. By the addition of wetting and/or dispersing agents, such pulverous compositions can be made readily wettable with water so that they can be converted into aqueous suspensions which are suitable, for example, as spray compositions.

The compounds of formula I can be mixed with a surface active agent and a solid carrier material to form a wettable powder which is dispersible in water, or they can be mixed with a solid pre-granulated carrier material to form a granulate.

For preparation of emulsifiable concentrates which are especially suitable for storage and shipment, the active ingredient can be dissolved in a water-immiscible solvent, such as, for example, an alicyclic ketone, which conveniently contains a dissolved emulsifying agent, so that the solution becomes self-emulsifying upon addition to water. Alternatively, the active ingredient can be mixed with an emulsifying agent, and the mixture can then be diluted with water to the desired concentration. Moreover, the active substance can be dissolved in a solvent, and thereafter the solution can be mixed with an emulsifying agent. Such a mixture can likewise be diluted with water to the desired concentration. In this manner there are obtained emulsifiable concentrates or ready-for-use emulsions.

The pesticidal compositions of this invention generally contain between 0.0005 percent by weight and 95 percent by weight of compound or compounds of formula I as active ingredient, preferably between 1 percent by weight and 75 percent by weight.

The pesticidal compositions of the present invention can be in forms suitable for storage or shipment. In such forms (e.g., emulsifiable concentrates), the concentration of active ingredients is normally at the higher end of the above concentration range. These forms can then be diluted with the same or different carrier materials to afford active ingredient concentrations suitable for practical use, and such concentrations normally lie at the lower end of the above-noted concentration range. Emulsifiable concentrates generally contain from about 5 percent by weight to about 95 percent by weight of the compound or compounds of formula I, preferably from about 10 percent by weight to about 75 percent by weight.

The application forms prepared from the above-indicated compositions include ready-for-use solutions, emulsions, foams, suspensions, powders, pastes, soluble powders, dusting agents and granulates.

The concentrations of active ingredient in the ready-for-use preparations can vary over wide limits. In spray liquors, the concentration can be, for example, between 0.0005 percent by weight and 20 percent by weight.

The active ingredients can also be used with good effect in the ultra-low-volume process (ULV) where it is possible to formulate spray liquors having preferably from about 10 to about 20 percent by weight of active ingredient.

The active ingredients can also be used with good effect in the low-volume process and in the high-volume process where it is possible to formulate spray liquors having from 0.5 to 1.0 and 0.05 to 0.1 percent by weight of active ingredient respectively.

In granulates which especially useful in mosquito control, the concentration of active ingredient is preferably from about 2 to about 10 percent by weight of the compound or compounds of formula I as the active ingredient.

The present invention is also concerned with a method for the treatment of the locus to be protected or the pests themselves with a compound of this invention or with the pesticidal compositions of the present invention. This method of use is preferably carried out by applying the composition to the soil or leaves, or by application to animals, provisions, or materials to be protected, depending on the pests to be controlled. The control is achieved e.g. by contact or by intake with feed.

The pesticidal compositions can be applied in a conventional manner, such as by sprinkling, spraying, smoke-screening, dusting, scattering, drilling-in, vaporizing, pouring, soaking or incrustating. Pulverous preparations can be applied to the pests or to the objects to be protected, such as plants or animals, as, for example, dusting agents using the usual dusting apparatuses.

Aqueous suspensions can be used, for example, as spray compositions.

The following Examples illustrate the present invention in more detail:

I. Manufacture of the active substances of formula I:

EXAMPLE 1

8.0 g (0.043 mol) of 6-ethoxy-4-chloromethyl-2-methyl-pyrimidine and 10.8 g (0.045 mol) of potassium O-ethyl S-(n-propyl) dithiophosphate are suspended in 20 ml of acetone. After the addition of a small amount (spatula tip) of sodium iodide the mixture is stirred well at 45° C. for 12 hours. The mixture is then filtered through Celite, the filtrate is concentrated under reduced pressure and the thus-isolated solid is taken up in 100 ml of toluene. The toluene solution is washed once with 5% sodium carbonate solution and once with saturated sodium chloride solution and dried over anhydrous sodium sulphate, and the solvent is removed by evaporation at 60° C. under reduced pressure. In this manner there is obtained O-ethyl S-(6-ethoxy-2-methyl-4-pyrimidinylmethyl) S-(n-propyl) dithiophosphate as an almost colourless oil, $n_D^{20}$ 1.5385.

EXAMPLE 2

A small amount (spatula tip) of sodium iodide is added to a solution of 15 g (0.070 mol) of 4-chloromethyl-2,6-diethoxy-pyrimidine and 18 g (0.070 mol) of dimethylammonium O-ethyl S-(n-propyl) dithiophosphate in 40 ml of ethanol and the mixture is stirred at 45°–50° C. for 16 hours. The mixture is subsequently taken up in 150 ml of toluene and the toluene solution is washed once with saturated sodium bicarbonate solution and once with saturated sodium chloride solution and dried over anhydrous sodium sulphate. The solvent is removed by evaporation under reduced pressure and the resulting slightly reddish oil is filtered through silica gel. In this manner there is obtained O-ethyl S-(2,6-diethoxy-4-pyrimidinylmethyl) s-(n-propyl) dithiophosphate as an almost colourless oil, $n_D^{26}$ 1.5333.

EXAMPLES 3–55

The corresponding starting materials of formulae II and III are reacted analogously to the process described in Example 1 or Example 2 in order to manufacture the compounds of formula I, in particular the compounds of formulae Ia and Ib given below, listed in Tables 1 and 2 hereinafter.

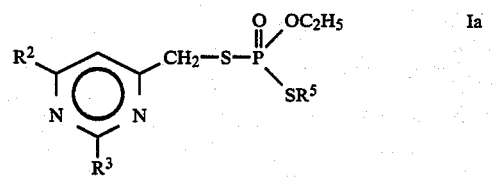

TABLE 1

| Ex. | R² | R³ | R⁵ | Physical data |
|---|---|---|---|---|
| 3 | OC₂H₅ | CH₃ | sec.C₄H₉ | $n_D^{25}$ = 1.5360 |
| 4 | OC₂H₅ | ▷ (cyclopropyl) | nC₃H₇ | $n_D^{20}$ = 1.5483 |
| 5 | Cl | tert.C₄H₉ | nC₃H₇ | $n_D^{20}$ = 1.5414 |
| 6 | OC₂H₅ | OC₂H₅ | sec.C₄H₉ | $n_D^{20}$ = 1.5354 |
| 7 | OC₂H₅ | tert.C₄H₉ | nC₃H₇ | $n_D^{22}$ = 1.5241 |
| 8 | OCH₃ | tert.C₄H₉ | nC₃H₇ | $n_D^{24}$ = 1.5234 |

TABLE 1-continued

| Ex. | R² | R³ | R⁵ | Physical data |
|---|---|---|---|---|
| 9 | N(CH₃)₂ | Cl | nC₃H₇ | oil ¹H—NMR (CDCl₃): 3.15 (s,N(CH₃)₂) 3.96 (d,CH₂SP), 6.52 (s, CH); |
| 10 | Cl | Cl | nC₃H₇ | $n_D^{23} = 1.5702$ |
| 11 | OCH₃ | Cl | nC₃H₇ | $n_D^{23} = 1.5598$ |
| 12 | Cl | isoC₃H₇ | nC₃H₇ | $n_D^{21} = 1.5473$ |
| 13 | OC₂H₅ | isoC₃H₇ | nC₃H₇ | $n_D^{21} = 1.5290$ |
| 14 | OCH₃ | OCH₃ | nC₃H₇ | $n_D^{21} = 1.5469$ |
| 15 | Cl | C₂H₅ | nC₃H₇ | $n_D^{23} = 1.5513$ |
| 16 | OCH₂CH₃ | C₂H₅ | nC₃H₇ | $n_D^{23} = 1.5346$ |
| 17 | OCON(CH₃)₂ | CH₃ | nC₃H₇ | $n_D^{27} = 1.5408$ |
| 18 | OP(S)(OCH₃)₂ | CH₃ | nC₃H₇ | $n_D^{22} = 1.5459$ |
| 19 | OC₂H₅ | SCH₃ | nC₃H₇ | $n_D^{22} = 1.5612$ |
| 20 | SC₂H₅ | ◁ | nC₃H₇ | $n_D^{24} = 1.5741$ |
| 21 | isoC₃H₇O | isoC₃H₇O | nC₃H₇ | $n_D^{23} = 1.5272$ |
| 22 | isoC₃H₇O | isoC₃H₇ | nC₃H₇ | $n_D^{22} = 1.5246$ |
| 23 | OCH₂C≡CH | isoC₃H₇ | nC₃H₇ | $n_D^{23} = 1.5396$ |
| 24 | OCH₂CH=CH₂ | isoC₃H₇ | nC₃H₇ | $n_D^{25} = 1.5332$ |
| 25 | OC₂H₅ | Cl | nC₃H₇ | $n_D^{24} = 1.5422$ |
| 26 | SC₂H₅ | SC₂H₅ | nC₃H₇ | $n_D^{26} = 1.5914$ |
| 27 | OC₂H₅ | —C₆H₄—Cl—p | nC₃H₇ | $n_D^{23} = 1.5840$ |
| 28 | OP(S)(OC₂H₅)₂ | —C₆H₄—Cl—p | nC₃H₇ | oil ¹H—NMR (CDCl₃): 4.23 (d,CH₂SP), 7.03 (s,CH), 7.47 (d,CH), 8.43 (d,CH) |
| 29 | OC₂H₅ | OC₂H₅ | C₂H₅ | $n_D^{20} = 1.5323$ |
| 30 | OCSN(CH₃)₂ | CH₃ | nC₃H₇ | oil ¹H—NMR (CDCl₃): 2.78 (s,CH₃), 3.08 (s,N(CH₃)₂), 4.12 (d,CH₂SP), 7.87 (s,CH) |
| 31 | OC₆H₅ | CH₃ | nC₃H₇ | $n_D^{25} = 1.5749$ |
| 32 | N(CH₃)₂ | CH₃ | nC₃H₇ | oil ¹H—NMR (CDCl₃): 2.50 (s,CH₃), 3.10 (s,N(CH₃)₂), 3.97 (d,CH₂SP), 6.40 (s,CH) |
| 33 | OCON(CH₃)₂ | OC₂H₅ | nC₃H₇ | $n_D^{24} = 1.5410$ |
| 34 | Cl | N(C₂H₅)₂ | nC₃H₇ | $n_D^{24} = 1.5623$ |
| 35 | Cl | NHC₃H₇iso | nC₃H₇ | $n_D^{24} = 1.5659$ |
| 36 | N(C₂H₅)₂ | Cl | nC₃H₇ | $n_D^{24} = 1.5684$ |
| 37 | NHC₃H₇iso | Cl | nC₃H₇ | $n_D^{25} = 1.5689$ |
| 38 | OCH₂C≡CH | isoC₃H₇ | sec.C₄H₉ | $n_D^{24} = 1.5367$ |
| 39 | OC₂H₅ | OCH₃ | nC₃H₇ | $n_D^{20} = 1.5424$ |
| 40 | OCH₂C≡CH | OCH₃ | nC₃H₇ | $n_D^{25} = 1.5536$ |
| 41 | N(C₂H₅)₂ | OCH₃ | nC₃H₇ | $n_D^{25} = 1.5528$ |
| 42 | OC₂H₅ | N(C₂H₅)₂ | nC₃H₇ | oil ¹H—NMR (CDCl₃): 3.70 (q,N(CH₂—CH₃)₂), 3.90 (d, CH₂SP), 4.33 (q, OCH₂CH₃), 5.95 (s,CH) |
| 43 | isoC₃H₇O | OCH₃ | nC₃H₇ | oil ¹H—NMR (CDCl₃): 1.37 (d,CH(CH₃)₂), 4.00 (s,OCH₃), 4.03 (d,CH₂SP), 5.39 (m,CH(CH₃)₂), 6.42 (s,CH) |
| 44 | OCH₃ | H | nC₃H₇ | $n_D^{25} = 1.5465$ |
| 45 | OC₂H₅ | H | nC₃H₇ | $n_D^{25} = 1.5400$ |
| 46 | OCH₂C≡CH | H | nC₃H₇ | $n_D^{25} = 1.5541$ |
| 47 | OC₆H₅ | H | nC₃H₇ | $n_D^{25} = 1.5784$ |
| 48 | CH₃ | isoC₃H₇ | nC₃H₇ | $n_D^{24} = 1.5353$ |
| 49 | OCH₂CH₂OCH₃ | isoC₃H₇ | nC₃H₇ | oil ¹H—NMR (CDCl₃): 1.28 (d,CH(CH₃)₂), 3.07 (m,CH(CH₃)₂), 3.40 (s,OCH₃), 3.75 (m,OCH₂), 4.07 (d,CH₂SP), 4.56 (m,OCH₂), 6.70 (s,CH) |
| 50 | F | isoC₃H₇ | nC₃H₇ | oil ¹H—NMR (CDCl₃): 1.33 (d,CH(CH₃)₂), 3.18 (m,CH(CH₃)₂), 4.20 (d,CH₂SP), 6.98 (d,J$_{HF}$ = 2Hz,H), |
| 51 | F | Cl | nC₃H₇ | ¹H—NMR (CDCl₃): 4.17 (d,CH₂SP), 7.20 (d,J$_{HF}$ = 2HZ,H); $n_D^{22} = 1.5410$ |
| 52 | OC₃H₇iso | OC₂H₅ | nC₃H₇ | $n_D^{21} = 1.5360$ |

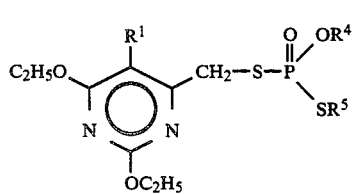

TABLE 2

| Ex. | R¹ | R⁴ | R⁵ | Physical data |
|---|---|---|---|---|
| 53 | H | CH₃ | CH₃ | oil ¹H—NMR (CDCl₃): 2.10 (d,CH₃SP), 3.73 (d, CH₃OP), 4.00 (d,CH₂SP), 4.42 (q,OCH₂CH₃), 6.43 (s,CH) |
| 54 | H | CH₃ | nC₃H₇ | $n_D^{26} = 1.5412$ |
| 55 | Cl | C₂H₅ | nC₃H₇ | $n_D^{24} = 1.5449$ |

EXAMPLE 56

2 g (0.053 mol) of O-ethyl S-(2,6-diethoxy-4-pyrimidinylmethyl) S-(n-propyl) dithiophosphate (see Example 2) and 0.3 g (0.0145 mol) of phosphorus pentasulphide in 10 ml of toluene are left at 60° C. for 16 hours. The mixture is then diluted with 50 ml of toluene and the solution is washed once with 0.5N hydrochloric acid and twice with saturated sodium chloride solution. The solvent is subsequently removed by evaporation under reduced pressure and the resulting crude product is purified by chromatography on silica gel with 15% diethyl ether in n-hexane. There is obtained O-ethyl S-(2,6-diethoxy-4-pyrimidinylmethyl) S-(n-propyl) trithiophosphate as a yellow oil, $n_D^{23}$ 1.5648.

EXAMPLE 57

O-Ethyl S-(2,6-dichloro-4-pyrimidinylmethyl) S-(n-propyl) dithiophosphate (see Example 10) is sulphurized with phosphorus pentasulphide analogously to the process described in Example 56 in order to manufacture O-ethyl S-(2,6-dichloro-4-pyrimidinylmethyl) S-(n-propyl) trithiophosphate, $n_D^{23}$ 1.6063.

EXAMPLE 58

S-(6-ethoxy-2-methyl-4-pyrimidinylmethyl) O-ethyl S-(sec.butyl) dithiophosphate (see Example 3) is sulphurized with phosphorus pentasulphide analogously to the process described in Example 56 in order to manufacture S-(6-ethoxy-2-methyl-4-pyrimidinylmethyl) O-ethyl S-(sec.butyl) trithiophosphate, $n_D^{20}$ 1.5691.

II Preparation of the starting materials:

EXAMPLE 59

The 6-ethoxy-4-chloromethyl-2-methyl-pyrimidine required as the starting material in Examples 1 and 3 can be produced as follows:

15.8 g (0.1 mol) of 6-chloromethyl-4-hydroxy-2-methyl-pyrimidine, 13 ml (0.1 mol) of diethyl sulphate and 27.6 g (0.2 mol) of potassium carbonate are heated at reflux in 500 ml of acetone for 6 hours. The mixture is then filtered and the filtrate is concentrated to dryness. The residue is taken up in 200 ml of methylene chloride and the methylene chloride solution is washed once with 50 ml of 2N sodium hydroxide and twice with 50 ml of semi-saturated sodium chloride solution, dried over anhydrous sodium sulphate and evaporated under reduced pressure. The residual oil is distilled at 47° C./0.07 mmHg, whereupon the distillate becomes solid. There is obtained 6-ethoxy-4-chloromethyl-2-methyl-pyrimidine, m.p. 29° C.

EXAMPLE 60

The 4-chloromethyl-2,6-diethoxy-pyrimidine required as the starting material in Examples 2, 6, 29, 53 and 54 can be produced as follows:

16.1 g (0.1 mol) of 6-chloromethyl-uracil and 57.0 g (0.3 mol) of triethyloxonium tetrafluoroborate are suspended in 100 ml of 1,1,2-trichloroethane and the suspension is left at 90° C. for 18 hours. The mixture is subsequently cooled and treated dropwise with a 50% aqueous solution of 41.5 g (0.3 mol) of potassium carbonate, incipient strong evolution of carbon dioxide being observed. The supernatant is then decanted off from the precipitated sludge-like residue and the residue is extracted several times with small amounts of methylene chloride. The combined organic phases are washed with water, dried over anhydrous sodium sulphate and evaporated under reduced pressure. The crude product is taken up in hot n-hexane and the solution is treated with active carbon and separated from insoluble constituents by filtration. Upon concentration of the filtrate there is obtained 4-chloromethyl-2,6-diethoxy-pyrimidine, m.p. 38°–39° C.

EXAMPLE 61

The 6-chloro-4-chloromethyl-2-isopropyl-pyrimidine required as the starting material in Example 12 can be produced as follows:

12.1 g (0.065 mol) of 4-chloromethyl-6-hydroxy-2-isopropyl-pyrimidine are suspended in 50 ml of phosphorus oxychloride and the suspension is heated to 80° C. for 30 minutes under nitrogen, the crystalline starting material dissolving gradually. The excess phosphorus oxychloride is then distilled off at 40°–60° C. under reduced pressure. The residue is poured on to ice-water, the pH-value of the mixture is brought to 7 by the addition of sodium hydroxide and the mixture is extracted three times with diethyl ether. The combined organic extracts are dried over anhydrous sodium sulphate and evaporated under reduced pressure. The dark coloured oily residue is taken up in hot n-hexane and the solution is treated with active carbon. After filtration of the hot mixture through Celite there is obtained 6-chloro-4-chloromethyl-2-isopropyl-pyrimidine as an orange oil which is pure in accordance with thin-layer chromatography. By distillation of this oil under reduced pressure there is obtained a colourless liquid, b.p. 75° C./0.05 mmHg, $n_D^{20}$ 1.5226.

EXAMPLE 62

The 6-ethoxy-4-chloromethyl-2-isopropyl-pyrimidine required as the starting material in Example 13 can be produced as follows:

A solution of 9.6 g (0.047 mol) of 6-chloro-4-chloromethyl-2-isopropyl-pyrimidine (see Example 61) in 40 ml of absolute ethanol is treated dropwise during 3 hours at 0° C. with a solution of 1.24 g (0.054 mol) of sodium in ethanol and the mixture is stirred at 0° C. for 3 hours and then at room temperature for 16 hours. The mixture is then taken up in diethyl ether and the solution is washed neutral with sodium chloride solution, dried over anhydrous sodium sulphate and freed from solvent under reduced pressure. After distillation of the oily residue in a high vacuum there is obtained 6-ethoxy-4-chloromethyl-2-isopropyl-pyrimidine, b.p. 52° C./0.07 mmHg, $n_D^{21}$ 1.4955.

EXAMPLES 63–71

The starting materials of formula II, in particular the starting materials of formula IIa given below, listed in Table 3 hereinafter are produced from the corresponding 2-alkyl-, 2-cycloalkyl-, 2-aryl- or 2-alkoxy-4-chloromethyl-6-hydroxy-pyrimidine or from 4-chloromethyl-6-hydroxy-pyrimidine analogously to the process described in Example 59 or 60 or to the process described in Examples 61 and 62. The corresponding products of formula I are also given in this Table.

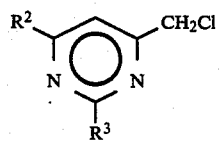

TABLE 3

| Ex. | R² | R³ | Physical data | Ex. No. of the product of formula I |
|---|---|---|---|---|
| 63 | OC₂H₅ | ▷ | b.p. 74° C./0.01 mmHg, $n_D^{20}$ = 1.5270 | 4 |
| 64 | OC₂H₅ | tert.C₄H₉ | oil ¹H—NMR (CDCl₃): 1.37 (s, C(CH₃)₃), 1.40 (t, CH₃), 4.44 (q,CH₂), 4.50 (s,CH₂Cl), 6.69 (s,CH) | 7 |
| 65 | OCH₃ | tert.C₄H₉ | b.p. 60° C./0.02 mmHg $n_D^{23}$ = 1.4933 | 8 |
| 66 | OC₂H₅ | C₂H₅ | oil ¹H—NMR (CDCl₃): 1.30 + 1.39 (tt,2 × CH₃), 2.75 + 4.42 (qq,2 × CH₂), 4.50 (s,CH₂Cl), 6.71 (s, CH) | 16 |
| 67 | OC₂H₅ | —C₆H₄—Cl—p | m.p. 83–84.5° C. | 27 |
| 68 | OC₂H₅ | OCH₃ | (oil) | 39 |
| 69 | isoC₃H₇O | OCH₃ | oil ¹H—NMR (CDCl₃): 1.35 (d,CH(CH₃)₂), 3.97 (s,OCH₃), 4.44 (s,CH₂Cl), 5.40 (m,CH(CH₃)₂), 6.50 (s,CH) | 43 |
| 70 | OCH₃ | H | oil ¹H—NMR (CDCl₃): 4.00 (s,OCH₃), 4.53 (s,CH₂Cl), 6.98 (s,CH), 8.75 (s,CH) | 44 |
| 71 | OC₂H₅ | H | oil ¹H—NMR (CDCl₃): 1.40 (t,OCH₂CH₃), 4.45 (q,OCH₂CH₃), 6.90 (s,CH), 8.75 (s,CH) | 45 |

EXAMPLES 72–78

The corresponding 2-alkyl- or 2-alkoxy-4-chloromethyl-6-hydroxy-pyrimidine, 6-chloromethyl-uracil or 4-chloromethyl-6-hydroxy-pyrimidine is treated with phosphorus oxychloride analogously to the process described in Example 61 in order to produce the starting materials of formula II, especially the starting materials of formula IIb given below, listed in Table 4 hereinafter. The corresponding products of formula I and the intermediates of formula II produced therefrom are also given in this Table.

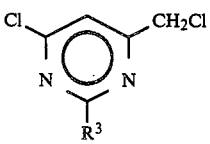

IIb

TABLE 4

| Ex. | R³ | Physical data | Example No. of the product of formula I or of the intermediate of formula II |
|---|---|---|---|
| 72 | tert.C₄H₉ | oil ¹H—NMR (CDCl₃): 1.40 (s,C(CH₃)₃), 4.63 (s,CH₂Cl), 7.43 (s,CH) | 5 |
| 73 | Cl | m.p. 32–33° C. b.p. 90° C./0.1 mmHg | 10 |
| 74 | C₂H₅ | b.p. 60° C./0.1 mmHg | 15 |
| 75 | CH₃ | oil $n_D^{22.5}$ = 1.5453 | 81,100 |
| 76 | OC₂H₅ | oil $n_D^{22.5}$ = 1.5362 | |
| 77 | OCH₃ | - (solid) | 82,103 |
| 78 | H | - (oil) | 83,84 |

EXAMPLE 79

6-Chloro-4-chloromethyl-2-isopropyl-pyrimidine (see Example 61) is reacted with isopropanol and sodium analogously to the process described in Example 62 in order to produce 4-chloromethyl-2-isopropyl-6-isopropoxy-pyrimidine which is required as the starting material in Example 22. This product is obtained in the form of an oil, ¹H-NMR (CDCl₃): 1.30 (d, 2×CH₃), 1.37 (d, 2×CH₃), 3.10 (m, CH), 4.50 (s, CH), 5.40 (m, CH), 6.65 (s, CH).

EXAMPLE 80

The 4-chloromethyl-2-isopropyl-6-(2-propynyloxy)-pyrimidine required as the starting material in Examples 23 and 38 can be produced as follows:

21.5 g of 50% sodium hydride dispersion in oil (0.45 mol of NaH) are suspended briefly in 200 ml of absolute n-pentane under nitrogen. The sodium hydride is then liberated from the oil by decantation and covered with 400 ml of dry tetrahydrofuran. 25.4 ml (0.43 mol) of 2-propynol are then introduced while stirring well, the temperature of the mixture rising to 40° C. After completion of the hydrogen evolution the mixture is cooled to 0° C. and a solution of 6-chloro-4-chloromethyl-2-isopropyl-pyrimidine (see Example 61) in 100 ml of tetrahydrofuran is added dropwise during 30 minutes. The mixture is stirred for 16 hours and the major part of the solvent is then removed by evaporation under reduced pressure. The residue is subsequently taken up in 300 ml of methylene chloride and the solution is washed neutral twice with 300 ml of water each time. The organic phase is dried over anhydrous magnesium sulphate and concentrated and the reaction is purified on silica gel with diethyl ether/n-hexane (1:9). In this manner there is obtained 4-chloromethyl-2-isopropyl-6-(2-propynyloxy)-pyrimidine in the form of a yellowish oil, $n_D^{24}$ 1.5142.

EXAMPLES 81–85

The starting materials of formula II listed in Table 5 hereinafter, especially the starting materials of formula IIa given above, are produced analogously to the process described in Example 80 from the corresponding 2-alkyl- or 2-alkoxy-6-chloro-4-chloromethyl-pyrimidine or 6-chloro-4-chloromethyl-pyrimidine and phenol, 2-propynol or ethylene glycol monomethyl ether. The corresponding products of formula I are also given in this Table.

TABLE 5

| Ex | R² | R³ | Physical data | Example No. of the product of formula I |
|---|---|---|---|---|
| 81 | OC₆H₅ | CH₃ | m.p. 48–50° C. | 31 |
| 82 | OCH₂C≡CH | OCH₃ | - (oil) | 40 |

TABLE 5-continued

| Ex | R² | R³ | Physical data | Example No. of the product of formula I |
|---|---|---|---|---|
| 83 | OCH₂C≡CH | H | m.p. 40–41° C. | 46 |
| 84 | OC₆H₅ | H | oil<br>¹H—NMR (CDCl₃)<br>4.62 (s,CH₂Cl), 7.0–7.7 (broad signal, C₆H₅ + 5-H in the pyrimidine nucleus), 8.80 (s,CH) | 47 |
| 85 | OCH₂CH₂OCH₃ | isoC₃H₇ | oil<br>¹H—NMR (CDCl₃):<br>1.30 (d,CH(CH₃)₂),<br>3.06 (m,CH(CH₃)₂),<br>3.44 (s,OCH₃), 3.75 (m,OCH₂), 4.52 (s, CH₂Cl), 4.58 (m, OCH₂), 6.80 (s,CH) | 49 |

EXAMPLE 86

The 4-chloromethyl-2-methyl-6-pyrimidinyl N,N-dimethylcarbamate required as the starting material in Example 17 can be produced as follows:

5 g (0.0315 mol) of 4-chloromethyl-6-hydroxy-2-methyl-pyrimidine are introduced portionwise under nitrogen into a suspension of 0.80 g (0.0331 mol) of sodium hydride (freed from a 50% dispersion in oil by two-fold extraction with n-pentane) in 50 ml of absolute tetrahydrofuran. After completion of the hydrogen evolution 2.9 ml (0.0315 mol) of dimethylcarbamoyl chloride are added dropwise and the mixture is heated at reflux for 16 hours. The cooled mixture is subsequently diluted with 150 ml of toluene, washed in succession with in each case 50 ml of 5% sodium bicarbonate solution, 0.1N hydrochloric acid and saturated sodium chloride solution, dried over anhydrous sodium sulphate and concentrated under reduced pressure. The residual oil is filtered briefly on silica gel with 90% diethyl ether in n-hexane. There is obtained 4-chloromethyl-2-methyl-6-pyrimidinyl N,N-dimethylcarbamate as a colourless oil, $n_D^{22}$ 1.5265.

EXAMPLE 87

The 4-chloromethyl-2-methyl-6-pyrimidinyl N,N-dimethyl-carbamate required as the starting material in Example 17 can also be produced as follows:

1.9 kg (12 mol) of 4-chloromethyl-6-hydroxy-2-methyl-pyrimidine are suspended in 14 l of toluene and treated in succession with 1.353 kg (12.6 mol) of dimethylcarbamoyl chloride and 3.48 kg (25.2 mol) of potassium carbonate. The pale beige suspension is subsequently stirred at 60° C. for 72 hours. The mixture is filtered through Celite and the toluene phase is washed four times with 5 l of 1% sulphuric acid each time, washed neutral twice with water and dried over anhydrous sodium sulphate The solvent is distilled off under reduced pressure, and there is thus obtained 4-chloromethyl-2-methyl-6-pyrimidinyl N,N-dimethyl-carbamate as a yellow oil. This crude product is purified by chromatography on 12 kg of silica gel with ethyl acetate/n-hexane (1:4) and recrystallized from diethyl ether/n-hexane. The purer product is obtained as white crystals, m.p. 49.5°–50° C.

EXAMPLE 68

4-Chloromethyl-6-hydroxy-2-isopropyl-pyrimidine is reacted with allylbromide analogously to the process described in Example 86 in order to produce 4-chloromethyl-2-isopropyl-6-(2-propenyloxy)-pyrimidine which is required as the starting material in Example 24. This product is obtained in the form of an oil, ¹H-NMR (CDCl₃): 1.30 (d, 2×CH₃), 3.15 (m, CH), 4.55 (s, CH₂), 4.93 (m, CH₂), 5.37 (m, CH₂), 6.12 (m, CH), 6.75 (s, CH).

EXAMPLE 89

4-Chloromethyl-6-hydroxy-2-methyl-pyrimidine is reacted with N,N-dimethylthiocarbamoyl chloride analogously to the process described in Example 86 in order to produce 4-chloromethyl-2-methyl-6-pyrimidinyl N,N-dimethylthiocarbamate which is required as the starting material in Example 30. This product is obtained in the form of a yellow oil.

EXAMPLE 90

2-Ethoxy-4-chloromethyl-6-hydroxy-pyrimidine is reacted with N,N-dimethylcarbamoyl chloride analogously to the process described in Example 87 in order to produce 2-ethoxy-4-chloromethyl-6-pyrimidinyl N,N-dimethylcarbamate which is required as the starting material in Example 33. This product is obtained in the form of a yellow oil, ¹H-NMR (CDCl₃): 1.43 (t, OCH₂CH₃), 3.08 and 3.14 (2×s, CON(CH₃)₂), 4.40 (q, OCH₂CH₃), 4.50 (s, CH₂Cl), 7.00 (s, CH).

EXAMPLE 91

4-Chloromethyl-2-(p-chlorophenyl)-6-hydroxy-pyrimidine is reacted with O,O-diethyl thiophosphoric acid chloride analogously to the process described in Example 87 in order to produce O,O-diethyl O-[4-chloromethyl-2-(p-chlorophenyl)-6-pyrimidinyl]thiophosphate which is required as the starting material in Example 28. This product is obtained in the form of a white solid.

EXAMPLE 92

The 4-chloromethyl-2,6-dichloro-pyrimidine (see Example 73) required as the starting material in Example 10 can also be produced as follows:

200 g (1.25 mol) of 6-chloromethyl-uracil are suspended in 600 ml of phosphorus oxychloride and the suspension is heated at 80° C. for 6 hours under nitrogen. The mixture is then added dropwise to 21 l of water at 30°–40° C. and the aqueous mixture is extracted twice with 5 l of methylene chloride each time. The organic phase is washed with water and washed neutral with potassium carbonate solution, dried over anhydrous sodium sulphate and evaporated under reduced pressure. After distillation of the oily residue is a high vacuum there is obtained 4-chloromethyl-2,6-dichloro-pyrimidine, b.p. 90° C./0.1 mm Hg, m.p. 32°–33° C.

EXAMPLE 93

The 4-chloromethyl-2,6-diethoxy-pyrimidine (see Example 60) required as the starting material in Examples 2, 6, 29, 53 and 54 can also be produced as follows:

A solution of 11.73 g (0.51 mol) of sodium in 260 ml of ethanol is added dropwise while cooling with ice and stirring during 1 hour to a solution of 50 g (0.255 mol) of 4-chloromethyl-2,6-dichloro-pyrimidine (see Examples 73 and 92) in 170 ml of absolute ethanol. The mixture is stirred at room temperature for a further 5 hours and poured into water, and the aqueous mixture is extracted twice with 1 l of methylene chloride each time. The organic phase is concentrated under reduced pressure and the oily residue is distilled in a high vacuum. There is thus obtained 4-chloromethyl-2,6-diethoxy-pyrimidine, b.p. 90° C./0.1 mm Hg and m.p. 38°–39° C.

EXAMPLES 94–97

The starting materials of formula II, in particular the starting materials of formula IIa given above, listed in Table 6 hereinafter are produced analogously to the process described in Example 93 from 4-chloromethyl-2,6-dichloro-pyrimidine (see Examples 73 and 92), the corresponding alcohol and sodium. The corresponding products of formula I are also given in this Table.

TABLE 6

| Ex. | $R^2$ | $R^3$ | Physical data | Ex. No. of the product of formula I |
|---|---|---|---|---|
| 94 | $OCH_3$ | Cl | - (oil) | 11 |
| 95 | $OCH_3$ | $OCH_3$ | - (oil) | 14 |
| 96 | isoC$_3$H$_7$O | isoC$_3$H$_7$O | oil $^1$H—NMR (CDCl$_3$): 1.34 (d, 2 × C$\underline{H}_3$), 1.40 (d, 2 × C$\underline{H}_3$), 4.42 (s,C$\underline{H}_2$) 5.22 (m,C$\underline{H}$), 5.36 (m,C$\underline{H}$), 6.44(s,C$\underline{H}$) | 21 |
| 97 | $OC_2H_5$ | Cl | - (oil) | 25 |

EXAMPLE 98

The 6-chloro-4-chloromethyl-2-diethylamino-pyrimidine and 2-chloro-4-chloromethyl-6-diethylamino-pyrimidine required as the starting materials in Examples 34 and 36 can be produced as follows:

A solution of 5.92 g (0.03 mol) of 4-chloromethyl-2,6-dichloro-pyrimidine (see Examples 73 and 92) in 60 ml of toluene is treated dropwise at 0° C. during 30 minutes with 12.5 ml (0.12 mol) of diethylamine. The mixture is subsequently left to come slowly to room temperature and it is then stirred for a further 24 hours. The mixture is diluted with 150 ml of toluene, the resulting mixture is washed with 50 ml of dilute sodium hydroxide solution and with water, the organic phase is dried over anhydrous magnesium sulphate and the solvent is removed by evaporation under reduced pressure.

By subjecting the crude product to chromatography on silica gel using diethyl ether/n-hexane (1:19) as the eluent there is obtained as the first fraction 6-chloro-4-chloromethyl-2-diethylamino-pyrimidine, which is required as the starting material in Example 34, in the form of an almost colourless oil, $^1$H-NMR (CDCl$_3$): 1.17 (t, N(CH$_2$CH$_3$)$_2$), 3.60 (q, N(CH$_2$CH$_3$)$_2$), 4.37 (s, CH$_2$Cl), 6.67 (s, CH).

By subsequent chromatography with diethyl ether/n-hexane (1:4) there is obtained as the main fraction 2-chloro-4-chloromethyl-6-diethylamino-pyrimidine, which is required as the starting material in Example 36, in the form of a yellow oil, $^1$H-NMR (CDCl$_3$): 1.20 (t, N(CH$_2$CH$_3$)$_2$), 3.54 (q, N(CH$_2$CH$_3$)$_2$), 4.44 (s, CH$_2$Cl), 6.48 (s, CH).

EXAMPLES 99–103

The corresponding 2-alkyl- or 2-alkoxy-6-chloro-4-chloromethyl-pyrimidine or 2-chloromethyl-2,6-dichloro-pyrimidine is reacted with the corresponding monoalkylamine or dialkylamine analogously to the process described in Example 98 in order to produce the starting materials of formula II, especially the starting materials of formula IIa given above, listed in Table 7 hereinafter. The corresponding products of formula I are also given in this Table.

TABLE 7

| Ex | $R^2$ | $R^3$ | Physical data | Example No. of the product of formula I |
|---|---|---|---|---|
| 99 | N(CH$_3$)$_2$ | Cl | - (oil) | 9 |
| 100 | N(CH$_3$)$_2$ | CH$_3$ | - (oil) | 32 |
| 101 | Cl | NHC$_3$H$_7$iso | oil $^1$H—NMR (CDCl$_3$): 1.22 (d,CH(C$\underline{H}_3$)$_2$), 4.22 (m,C$\underline{H}$(CH$_3$)$_2$), 4.37 (s,C$\underline{H}_2$Cl), 5.18 (broad signal, N$\underline{H}$), 6.70 (s,C$\underline{H}$) | 35 |
| 102 | NHC$_3$H$_7$iso | Cl | oil $^1$H—NMR (CDCl$_3$): 1.27 (d,CH(C$\underline{H}_3$)$_2$), 4.10 (m,C$\underline{H}$(CH$_3$)$_2$), 4.44 (s,C$\underline{H}_2$Cl), 5.28 (broad signal, N$\underline{H}$), 6.42 (s,C$\underline{H}$) | 37 |
| 103 | N(C$_2$H$_5$)$_2$ | OCH$_3$ | oil $^1$H—NMR (CDCl$_3$): 1.20 (t,N(CH$_2$C$\underline{H}_3$)$_2$), 3.53 (q,N(C$\underline{H}_2$CH$_3$)$_2$), 3.92 (s,OC$\underline{H}_3$), 4.40 (s, (C$\underline{H}_2$Cl), 6.22 (s,C$\underline{H}$) | 41 |

EXAMPLE 104

4-Ethoxy-2-chloro-6-chloromethyl-pyrimidine (see Example 97) is reacted with diethylamine analogously to the process described in Example 98 in order to produce 4-ethoxy-6-chloromethyl-2-diethylamino-pyrimidine which is required as the starting material in Example 42. This product is obtained in the form of a yellow oil, $^1$H-NMR (CDCl$_3$): 1.20 (t, N(CH$_2$CH$_3$)$_2$), 1.37 (t, OCH$_2$CH$_3$), 3.60 (q, N(CH$_2$CH$_3$)$_2$), 4.33 (s, CH$_2$Cl), 4.35 (q, OCH$_2$CH$_3$), 6.06 (s, CH).

EXAMPLE 105

The 4-chloromethyl-2,6-diethylthio-pyrimidine required as the starting material in Example 26 can be produced as follows:

A mixture of 16.05 g (0.10 mol) of 6-chloromethyl-uracil, 9.85 g (0.12 mol) of sodium acetate and 0.3 g of sodium iodide in 50 ml of glacial acetic acid is heated at reflux for 20 minutes. The mixture is subsequently cooled to room temperature and filtered. The filtrate is treated with 250 ml of diethyl ether and the resulting crystals are filtered off. The combined crystallizate is added to 200 ml of water and thus liberated from the residual salts. 11.3 g of 6-acetoxymethyl-uracil are isolated by filtration.

The product, dried at 50° C., of the first process step is dissolved in 73 ml (0.8 mol) of phosphorus oxychloride and the solution is heated at 80° C. for 1 hour. The excess phosphorus oxychloride is then distilled off under reduced pressure, the residue is poured into 200 ml of water, the aqueous mixture is extracted twice with 200 ml of diethyl ether each time, the combined extracts are dried over anhydrous sodium sulphate and the organic solution is evaporated. The oily residue is separated by chromatography with 25% diethyl ether in n-hexane. There is thus isolated 4-acetoxymethyl-2,6-dichloro-pyrimidine, $^1$H-NMR (CDCl$_3$): 2.23 (s, CH$_3$), 5.19 (s, CH$_2$), 7.35 (s, CH).

1.73 g (0.036 mol) of a 50% dispersion of sodium hydride in oil is introduced into 40 ml of absolute tetrahydrofuran and the resulting suspension is treated at room temperature with 2.54 ml (0.034 mol) of ethyl mercaptan. After completion of the hydrogen evolution a solution of 3.8 g of acetoxymethyl-2,6-dichloro-pyrimidine in 10 ml of tetrahydrofuran is added dropwise at 0° C. while cooling. The mixture is stirred at room temperature for 24 hours, subsequently diluted with 100 ml of diethyl ether and the diluted mixture is washed with saturated sodium chloride solution. The organic phase is then dried over anhydrous magnesium sulphate and evaporated. The oily residue is separated by chromatography on silica gel with 85% diethyl ether in n-hexane. There is thus isolated 4-acetoxymethyl-2,6-diethylthio-pyrimidine, $^1$H-NMR (CDCl$_3$): 1.39 (t, 2×CH$_3$), 2.19 (s, CH$_3$), 3.15 and 3.20 (qq, 2×CH$_2$), 5.01 (s, CH$_2$), 6.79 (s, CH).

A solution of 1.6 g (0.0059 mol) of 4-acetoxymethyl-2,6-diethylthio-pyrimidine in 3 ml of ethanol is treated at 0° C. with a solution of 0.86 g (0.0065 mol) of sodium hydroxide in 2.5 ml of ethanol. After 5 minutes the mixture is diluted with 150 ml of diethyl ether and washed neutral with water. The organic phase is dried over anhydrous magnesium sulphate and evaporated. In this manner there is obtained as the residue 2,6-diethylthio-4-hydroxymethyl-pyrimidine.

The residue (1.35 g) is then treated dropwise at 0° C. with 8.5 ml of thionyl chloride. After 10 minutes the excess thionyl chloride is distilled off under reduced pressure at 25° C. and the residue is extracted with 150 ml of diethyl ether and 50 ml of water. The organic phase is dried over anhydrous magnesium sulphate and the solvent is removed under reduced pressure. There are thus obtained 1.45 g of 4-chloromethyl-2,6-diethylthio-pyrimidine as a pale yellowish oil.

EXAMPLE 106

Analogously to the five-step process described in Example 105, from 4-chloromethyl-2-cyclopropyl-6-hydroxy-pyrimidine there is produced 6-ethylthio-4-chloromethyl-2-cyclopropyl-pyrimidine which is required as the starting material in Example 20. This product is obtained in the form of an oil.

EXAMPLE 107

4-Chloromethyl-6-hydroxy-2-methylthio-pyrimidine [known from S. Cohen et al., J.Org. Chem. 27, 3545–3549 (1962)] is treated with diethyl sulphate analogously to the process described in Example 59 in order to produce 6-ethoxy-4-chloromethyl-2-methylthio-pyrimidine which is required as the starting material in Example 19. M.p. (after crystallization from water) 167°–171° C.; $^1$H-NMR (CDCl$_3$): 1.40 (t, CH$_3$) 2.56 (s, SCH$_3$), 4.45 (q, CH$_2$), 4.47 (s, CH$_2$Cl), 6.55 (s, CH).

EXAMPLE 108

The 4-chloromethyl-2-isopropyl-6-methyl-pyrimidine required as the starting material in Example 48 can be produced as follows:

A mixture of 6.5 g (0.036 mol) of 4-hydroxy-2-isopropyl-6-methyl-pyrimidine and 16.8 g (0.108 mol) of phosphorus oxychloride in 40 ml of chloroform is heated at reflux for 2 hours. The solution is then concentrated under reduced pressure, the residue is poured into water and the aqueous phase is extracted twice with 100 ml of n-hexane each time. The organic phase is dried over anhydrous sodium sulphate and subsequently evaporated. There is obtained 4-chloro-2-isopropyl-6-methyl-pyrimidine in the form of an orange oil, $^1$H-NMR (CDCl$_3$): 1.32 (d, CH(CH$_3$)$_2$), 2.48 (s, CH$_3$), 3.17 (m, CH(CH$_3$)$_2$), 7.03 (s, CH).

3.05 g (0.018 mol) of the above product and 5.9 g (0.09 mol) of zinc powder are heated at reflux in 90 ml of water and thereafter treated dropwise with 1.4 ml (0.019 mol) of 25% ammonia solution. After a reaction time of 7 hours the mixture is cooled to room temperature and extracted twice with 100 ml of diethyl ether each time. The organic phase is dried over anhydrous sodium sulphate and the diethyl ether is distilled off over a Vigreux column under normal pressure. 2-Isopropyl-4-methyl-pyrimidine is obtained in the form of a yellowish oil.

1.7 g (0.0125 mol) of the above product are dissolved in a mixture of 9 ml of water, 22 ml of methanol and 0.91 ml of concentrated sulphuric acid and 5.6 g (0.0245 mol) of ammonium peroxydisulphate are subsequently added. The mixture is heated at reflux for 4 hours, thereafter concentrated under reduced pressure, water is added to the residue, the mixture is extracted with chloroform and the chloroform is removed from the organic phase by evaporation under reduced pressure. 4-Hydroxy-2-isopropyl-6-methyl-pyrimidine is obtained in the form of a brown oil.

A mixture of 1.7 g (0.0097 mol) of the above product, 10 ml of phosphorus oxychloride and 10 ml of chloroform is heated at reflux for 2 hours. The solvent and the excess phosphorus oxychloride are then distilled off under reduced pressure and the residue is poured into water. The aqueous phase is brought to a pH-value of 7 by the addition of dilute sodium hydroxide solution, the mixture is extracted twice with n-hexane, and the organic phase is dried with anhydrous sodium sulphate and evaporated. 4-Chloromethyl-2-isopropyl-6-methyl-pyrimidine is obtained as a yellowish oil, $^1$H-NMR (CDCl$_3$): 1.32 (d, CH(CH$_3$)$_2$), 2.53 (s, CH$_3$), 3.17 (m, CH(CH$_3$)$_2$), 4.53 (s, CH$_2$Cl), 7.20 (s, CH).

EXAMPLE 109

The 4-chloromethyl-6-fluoro-2-isopropyl-pyrimidine required as the starting material in Example 50 can be produced as follows:

A mixture of 0.8 g (0.0039 mol) of 6-chloro-4-chloromethyl-2-isopropyl-pyrimidine (see Example 61), 0.51 g (0.0089 mol) of anhydrous potassium fluoride and 0.14 g (0.0004 mol) of 18-crown-6 in 7 ml of acetonitrile is heated at reflux temperature for 48 hours. The mixture is then taken up in diethyl ether and the solution is washed with saturated sodium chloride solution, dried over anhydrous sodium sulphate and freed from solvent under reduced pressure. The 4-chloromethyl-6-fluoro-2-isopropyl-pyrimidine is obtained in the form of a yellow oil, $^1$H-NMR (CDCl$_3$): 1.32 (d, CH(CH$_3$)$_2$), 3.18 (m, CH(CH$_3$)$_2$), 4.62 (s, CH$_2$Cl), 6.99 (d, CH).

EXAMPLE 110

The 2-chloro-4-chloromethyl-6-fluoro-pyrimidine required as the starting material in Example 51 can be produced as follows:

5 g (0.027 mol) of 4-chloromethyl-2,6-dichloro-pyrimidine (see Examples 73 and 92) and 3.3 g (0.056 mol) of anhydrous potassium fluoride in 8 ml of sulpholane are heated at 140° C. for 24 hours. The mixture is then cooled to 0° C. and filtered over silica gel using diethyl ether/n-hexane (1:4). After removing the solvent by evaporation there is obtained 2-chloro-4-chloromethyl-6-fluoro-pyrimidine in the form of a yellow oil, $^1$H-NMR (CDCl$_3$): 4.70 (s, CH$_2$Cl), 7.30 (d, $J_{FH}$=2 Hz, H).

EXAMPLE 111

2-Ethoxy-5-chloro-4-chloromethyl-6-hydroxy-pyrimidine is converted analogously to the process described in Example 59 or 60 or to the process described in Examples 61 and 62 into 5-chloro-4-chloromethyl-2,6-diethoxy-pyrimidine which is required as the starting material in Example 55. This product is obtained in the form of an oil.

EXAMPLE 112

The 2-ethoxy-5-chloro-4-chloromethyl-6-hydroxy-pyrimidine required as the starting material in Example 111 can be produced as follows:

2.8 ml (0.035 mol) of sulphuryl chloride are added dropwise to a solution of 6 g (0.032 mol) of 2-ethoxy-4-chloromethyl-6-hydroxy-pyrimidine in 90 ml of methylene chloride and the mixture is subsequently stirred at room temperature for 4 hours. The mixture is then treated with 100 ml of water and adjusted to pH 7 with 30% sodium hydroxide solution. The organic phase is separated and the combined organic phases are extracted with water, dried over anhydrous sodium sulphate and evaporated. There is obtained crystalline 2-ethoxy-5-chloro-4-chloromethyl-6-hydroxy-pyrimidine, $^1$H-NMR (CDCl$_3$): 1.45 (t, OCH$_2$CH$_3$), 4.54 (q, OCH$_2$CH$_3$), 4.54 (s, CH$_2$Cl), 9.80 (broad signal, OH).

EXAMPLE 113

The 2-ethoxy-4-chloromethyl-6-hydroxy-pyrimidine required as the starting material in Examples 76, 90 and 112 as well as for the direct synthesis (by ethoxylation) of a 6-alkoxy-2-ethoxy-4-chloromethyl-pyrimidine (e.g. the product of Examples 60 and 93) can be produced as follows:

A mixture of 24.9 g (0.2 mol) of O-ethylisourea hydrochloride and 21.5 g (0.14 mol) of methyl 4-chloroacetoacetate in 100 ml of methanol is treated at 0°–5° C. during 10 minutes with a solution of 7.55 g (0.33 mol) of sodium in 100 ml of methanol. The mixture is stirred at 0° C. for 2 hours and at room temperature for 18 hours and the solvent is then removed by evaporation under reduced pressure. The residue is dissolved in 300 ml of water and the solution is adjusted to a pH-value of 6. The resulting crystallline product is filtered off, washed with diethyl ether and dried at 40° C. In this manner there is obtained 2-ethoxy-4-chloromethyl-6-hydroxy-pyrimidine, m.p. 157°–159° C. By back-extracting the aqueous filtrate three times with 150 ml of chloroform each time there is obtained an additional amount of this product, m.p. 159°–161° C.

EXAMPLE 114

The 2-ethoxy-4-chloromethyl-6-hydroxy-pyrimidine can also be produced as follows:

An emulsion of 20.9 g (0.135 mol) of methyl 4-chloroacetoacetate and 23.5 g (0.189 mol) of O-ethylisourea hydrochloride is treated with a solution of 41.3 g (0.31 mol) of sodium hydroxide in 40 ml of water at −20° C. to −10° C. during 5 minutes while stirring well. After stirring at room temperature for 2 hours the resulting crystalline product is filtered off and dried.

The crystals, m.p. 156°–158° C., are washed well with diethyl ether. There is obtained 2-ethoxy-4-chloromethyl-6-hydroxy-pyrimidine, m.p. 161°–163° C.

EXAMPLE 115

Analogously to the process described in Example 113, O-methylisourea hydrochloride or hydrosulphate is reacted with methyl 4-chloroacetoacetate in order to produce 4-chloromethyl-6-hydroxy-2-methoxy-pyrimidine, m.p. 154°–155° C., which is required as the starting material in Examples 68, 69 and 77.

EXAMPLE 116

Analogously to the process described in Example 113, formamidine hydroacetate or hydrochloride is reacted with methyl 4-chloroacetoacetate in order to produce 4-chloromethyl-6-hydroxy-pyrimidine, m.p. 164°–165.5° C. (crystallized from ethanol), which is required as the starting material in Examples 70, 71 and 78.

III. Formulation Examples:

EXAMPLE 117

An emulsifiable concentrate has the following composition:

|  | g/liter |
|---|---|
| Compound of formula I (active substance) | 500 |
| Emulsifier mixture consisting of calcium alkylaryl sulphonate, alkylphenol ethoxylate and an ethylene oxide/propylene oxide block polymerizate | 50 |
| Calcium dodecylbenzenesulphonate | 25 |
| Solvent [mixture of mono-, di- and tri(lower alkyl)benzenes] | ad 1000 ml |

We claim:
1. A compound of the formula

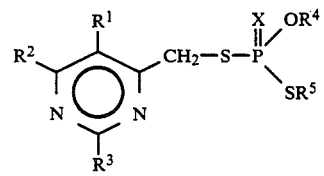

wherein R$^1$ is hydrogen, fluorine or chlorine, R$^2$ is hydrogen, fluorine, chlorine, C$_{1-4}$-alkyl, C$_{1-6}$-alkoxy, 2-propenyloxy, 2-propynyloxy, 2-(C$_{1-4}$-alkoxy)-ethoxy, unsubstituted phenoxy, phenoxy monosubstituted or disubstituted with halogen, C$_{1-6}$-alkylthio, C$_{1-4}$-alkylamino, di(C$_{1-4}$-alkyl)amino or a group (a) or (b)

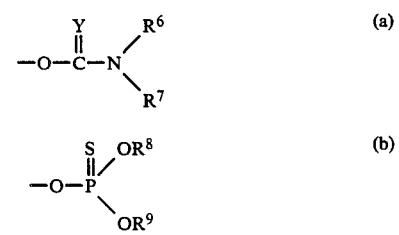

R$^3$ is hydrogen, fluorine, chlorine, C$_{1-6}$-alkyl, C$_{3-6}$-cycloalkyl, (C$_{1-4}$-alkoxy)methyl, (C$_{1-4}$-alkylthio)methyl, C$_{1-6}$-alkoxy, 2-propenyloxy, 2-propynyloxy, C$_{1-6}$alkylthio, C$_{1-4}$-alkylamino, di(C$_{1-4}$-alkyl)amino or unsubstituted, monosubstituted or disubstituted phenyl, the substituents being fluorine, chlorine, trifluoromethyl and/or methoxy, $R^4$ is $C_{1-3}$-alkyl, $R^5$ is n-propyl or sec.butyl, $R^6$, $R^7$, $R^8$ and $R^9$ each independently are $C_{1-3}$-alkyl and X and Y each independently are oxygen or sulfur.

2. The compound according to claim 1, wherein $R^2$ is hydrogen, fluorine, chlorine, $C_{1-4}$-alkyl, $C_{1-6}$-alkoxy, 2-propenyloxy, 2-propynyloxy, $C_{1-6}$-alkylthio, di($C_{1-4}$-alkyl)-amino or a group (a) or (b), $R^3$ is hydrogen, fluorine, chlorine, $C_{1-6}$-alkyl, $C_{3-6}$-cycloalkyl, ($C_{1-4}$-alkoxy)-methyl, ($C_{1-4}$-alkylthio)methyl, $C_{1-6}$-alkoxy, 2-propenyloxy, 2-propynyloxy, $C_{1-6}$-alkylthio, di($C_{1-4}$-alkyl)amino or unsubstituted, monosubstituted or disbustituted phenyl, the substituents being fluorine, chlorine, trifluoromethyl and/or methoxy, and $R^1$, $R^4$, $R^5$ and X are as defined in claim 1.

3. The compound according to claim 2, wherein $R^1$ is hydrogen.

4. The compound according to claim 3, wherein $R^2$ is methoxy, ethoxy, isopropoxy or 2-propynyloxy.

5. The compound according to of claim 4, wherein $R^3$ is hydrogen, methyl, isopropyl, tert.butyl, cyclopropyl, methoxy, ethoxy, methylthio, ethylthio, dimethylamino or diethylamino.

6. The compound according to claim 1, wherein $R^3$ is isopropylamino.

7. The compound according to claim 5, wherein $R^4$ is ethyl.

8. The compound according to claim 7, wherein $R^5$ is n-propyl.

9. The compound according to claim 8, wherein X is oxygen.

10. The compound according to claim 2, wherein $R^2$ and/or $R^3$ are $C_{1-6}$-alkoxy, 2-propenyloxy or 2-propynyloxy.

11. The compound according to claim 2, wherein $R^1$, $R^2$ and/or $R^3$ are chlorine.

12. The compound according to claim 1, wherein $R^2$ is 2-($C_{1-4}$-alkoxy)-ethoxy, unsubstituted phenoxy or phenoxy monosubstituted or disubstituted with halogen.

13. The compound according to claim 2, wherein $R^2$ and/or $R^3$ are $C_{1-6}$-alkylthio.

14. The compound according to claim 1, wherein $R^2$ and/or $R^3$ are $C_{1-4}$-alkylamino or di($C_{1-4}$-alkyl)amino.

15. The compound according to claim 2, wherein $R^2$ is $C_{1-4}$-alkyl and $R^3$ is $C_{1-6}$-alkyl, $C_{3-6}$-cycloalkyl, ($C_{1-4}$-alkoxy)methyl, $C_{1-6}$-alkoxy, di($C_{1-4}$-alkyl)amino or phenyl optionally substituted with methoxy.

16. The compound according to claim 2, wherein $R^1$, $R^2$ and/or $R^3$ are hydrogen.

17. The compound according to claim 2, wherein $R^1$, $R^2$ and/or $R^3$ are fluorine.

18. The compound according to claim 2, wherein $R^2$ is a group (a) or (b).

19. O-Ethyl S-(2,6-diethoxy-4-pyrimidinylmethyl) S-(n-propyl)dithiophosphate.

20. O-Ethyl S-[2-isopropyl-6-(2-propynyloxy)-4-pyrimidinylmethyl]S-(n-propyl)dithiophosphate.

21. A compound selected from the group consisting of

O-Ethyl S-(6-ethoxy-2-methyl-4-pyrimidinylmethyl) S-(n-propyl)dithiophosphate,

O-ethyl S-(sec.butyl) S-(6-ethoxy-2-methyl-4-pyrimidinylmethyl)dithiophosphate,

O-ethyl S-(6-ethoxy-2-cyclopropyl-4-pyrimidinylmethyl)S-(n-propyl)dithiophosphate, O-ethyl S-[2-(tert.butyl)-6-chloro-4-pyrimidinylmethyl]S-(n-propyl)dithiophosphate, O-ethyl-S-(sec.butyl)-S-(2,6-diethoxy-4-pyrimidinylmethyl)dithiophosphate, O-ethyl S-[6-ethoxy-2-(tert.butyl)-4-pyrimidinylmethyl]S-(n-propyl)dithiophosphate, O-ethyl S-[2-(tert.butyl)-6-methoxy-4-pyrimidinylmethyl]S-(n-propyl)dithiophosphate, O-ethyl S-(2-chloro-6-dimethylamino-4-pyrimidinylmethyl) S-(n-propyl)dithiophosphate, O-ethyl S-(2,6-dichloro-4-pyrimidinylmethyl) S-(n-propyl)dithiophosphate, O-ethyl S-(2-chloro-6-methoxy-4-pyrimidinylmethyl) S-(n-propyl)dithiophosphate, O-ethyl S-(6-chloro-2-isopropyl-4-pyrimidinylmethyl) S-(n-propyl)dithiophosphate, O-ethyl S-(2,6-dimethoxy-4-pyrimidinylmethyl) S-(n-propyl)dithiophosphate, O-ethyl S-(2-ethyl-6-chloro-4-pyrimidinylmethyl) S-(n-propyl)dithiophosphate, O-ethyl S-(6-ethoxy-2-ethyl-4-pyrimidinylmethyl) S-(n-propyl)dithiophosphate, O-ethyl S-(6-dimethylcarbamoyloxy-2-methyl-4-pyrimidinylmethyl) S-(n-propyl)dithiophosphate, O-ethyl S-[6-(O,O-dimethyl-thiophosphoro)-2-methyl-4-pyrimidinylmethyl]S-(n-propyl)dithiophosphate, O-ethyl S-(6-ethoxy-2-methylthio-4-pyrimidinylmethyl) S-(n-propyl)dithiophosphate, O-ethyl S-(6-ethylthio-2-cyclopropyl-4-pyrimidinylmethyl)S-(n-propyl)dithiophosphate, O-ethyl S-(2,6-diisopropoxy-4-pyrimidinylmethyl)S-(n-propyl)dithiophosphate, O-ethyl S-(6-isopropoxy-2-isopropyl-4-pyrimidinylmethyl)S-(n-propyl)dithiophosphate, O-ethyl S-[2-isopropyl-6-(2-propenyloxy)-4-pyrimidinylmethyl]S-(n-propyl)dithiophosphate, O-ethyl S-(6-ethoxy-2-isopropyl-4-pyrimidinylmethyl) S-(n-propyl)dithiophosphate, O-ethyl S-(6-ethoxy-2-chloro-4-pyrimidinylmethyl) S-(n-propyl)dithiophosphate, O-ethyl S-(2,6-diethylthio-4-pyrimidinylmethyl S-(n-propyl)dithiophosphate, O-ethyl S-[6-ethoxy-2-(p-chlorophenyl)-4-pyrimidinylmethyl]S-(n-propyl)dithiophosphate, O-ethyl S-(2,6-diethoxy-4-pyrimidinylmethyl) S-(n-propyl)trithiophosphate, O-ethyl S-(26-dichloro-4-pyrimidinylmethyl)S-(n-propyl)trithiophosphate and O-ethyl S-(6-ethoxy-2-methyl-4-pyrimidinylmethyl) S-(sec.butyl)trithiophosphate.

22. A compound selected from the group consisting of

O-Ethyl S-[2-(p-chlorophenyl)-6-(O,O-diethyl-thiophosphoro)-4-pyrimidinylmethyl]S-(n-propyl)dithiophosphate, O-ethyl-S-(6-dimethylthiocarbamoyloxy-2-methyl-4-pyrimidinylmethyl) S-(n-propyl)dithiophosphate, O-ethyl S-(2-methyl-6-phenoxy-4-pyrimidinylmethyl) S-(n-propyl)dithiophosphate, O-ethyl S-(6-dimethylamino-2-methyl-4-pyrimidinylmethyl)S-(n-propyl)dithiophosphate, O-ethyl S-(2-ethoxy-6-dimethylcarbamoyloxy-4-pyrimidinylmethyl) S-(n-propyl)dithiophosphate, O-ethyl S-(2-diethylamino-6-chloro-4-pyrimidinylmethyl) S-(n-propyl)dithiophosphate, O-ethyl S-(6-chloro-2-isopropylamino-4-pyrimidinylmethyl) S-(n-propyl)dithiophosphate, O-ethyl S-(2-chloro-6-diethylamino-4-pyrimidinylmethyl) S-(n-propyl)dithiophosphate,
O-ethyl S-(2-chloro-6-isopropylamino-4-pyrimidinylmethyl) S-(n-propyl)dithiophosphate,
O-ethyl S-(sec.butyl)S-[2-isopropyl-6-(2-propynyloxy)-4-pyrimidinylmethyl]dithiophosphate,
O-ethyl S-(6-ethoxy-2-methoxy-4-pyrimidinylmethyl) S-(n-propyl)dithiophosphate,
O-ethyl S-[2-methoxy-6-(2-propynyloxy)-4-pyrimidinylmethyl]S-(n-propyl)dithiophosphate,
O-ethyl S-(6-diethylamino-2-methoxy-4-pyrimidinylmethyl) S-(n-propyl)dithiophosphate,
O-ethyl S-(6-ethoxy-2-diethylamino-4-pyrimidinylmethyl) S-(n-propyl)dithiophosphate,
O-ethyl S-(6-isopropoxy-2-methoxy-4-pyrimidinylmethyl) S-(n-propyl)dithiophosphate,
O-ethyl S-(6-methoxy-4-pyrimidinylmethyl) S-(n-propyl)dithiophosphate,
O-ethyl S-(6-ethoxy-4-pyrimidinylmethyl) S-(n-propyl)dithiophosphate,
O-ethyl S-[6-(2-propynyloxy)-4-pyrimidinylmethyl]S-(n-propyl)dithiophosphate,
O-ethyl S-(6-phenoxy-4-pyrimidinylmethyl) S-(n-propyl)dithiophosphate,
O-ethyl S-(2-isopropyl-6-methyl-4-pyrimidinylmethyl) S-(n-propyl)dithiophosphate,
O-ethyl S-[2-isopropyl-6-(2-methoxyethoxy)-4-pyrimidinyl-methyl]S -(n-propyl)dithiophosphate
O-ethyl S-(6-fluoro-2-isopropyl-4-pyrimidinylmethyl) S-(n-propyl)dithiophosphate,
O-ethyl S-(2-chloro-6-fluoro-4-pyrimidinylmethyl) S-(n-propyl)dithiophosphate,
O-ethyl S-(2-ethoxy-6-isopropoxy-4-pyrimidinylmethyl) S-(n-propyl)dithiophosphate,
S-(2,6-diethoxy-4-pyrimidinylmethyl)O-methyl S-(n-propyl)dithiophosphate and
O-ethyl S-(5-chloro-2,6-diethoxy-4-pyrimidinylmethyl) S-(n-propyl)dithiophosphate.

23. A pesticidal composition for control of insects, mites and nematodes which comprises inert carrier material and, as the active ingredient, an amount, which is effective as a pesticide, of a compound of claim 1.

24. A pesticidal composition for control of insects, mites and nematodes which comprises inert carrier material and, as the active ingredient, an amount, which is effective as a pesticide, of a compound of claim 2.

25. A pesticidal composition for control of insects, mites and nematodes which comprises inert carrier material and, as the active ingredient, an amount, which is effective as a pesticide, of a compound of claim 19.

26. A pesticidal composition for control of insects, mites and nematodes which comprises inert carrier material and, as the active ingredient, an amount, which is effective as a pesticide, of a compound of claim 20.

27. A pesticidal composition for control of insects, mites and nematodes which comprises inert carrier material and, as the active ingredient, an amount, which is effective as a pesticide, of a compound of claim 21.

28. A pesticidal composition for control of insects, mites and nematodes which comprises inert carrier material and, as the active ingredient, an amount, which is effective as a pesticide, of a compound of claim 22.

29. A method for the control of insects, mites and nematodes which comprises applying, to the site to be treated or the pests themselves, an amount of the pesticidal composition of claim 23 which is effective in the control of pests.

30. A method for the control of insects, mites and nematodes which comprises applying, to the site to be treated or the pests themselves, an amount of the pesticidal composition of claim 24 which is effective in the control of pests.

31. A method for the control of insects, mites and nematodes which comprises applying, to the site to be treated or the pests themselves, an amount of the pesticidal composition of claim 25 which is effective in the control of pests.

32. A method for the control of insects, mites and nematodes which comprises applying, to the site to be treated or the pests themselves, an amount of the pesticidal composition of claim 26 which is effective in the control of pests.

33. A method for the control of insects, mites and nematodes which comprises applying, to the site to be treated or the pests themselves, an amount of the pesticidal composition of claim 27 which is effective in the control of pests.

34. A method for the control of insects, mites and nematodes which comprises applying, to the site to be treated or the pests themselves, an amount of the pesticidal composition of claim 28 which is effective in the control of pests.

* * * * *